United States Patent
Tian et al.

(10) Patent No.: US 11,672,859 B2
(45) Date of Patent: Jun. 13, 2023

(54) RECOMBINANT FUSION PROTEINS TARGETING CD47 AND PD-L1, PREPARATION AND USE THEREOF

(71) Applicant: IMMUNEONCO BIOPHARMACEUTICALS (SHANGHAI) INC., Shanghai (CN)

(72) Inventors: Wenzhi Tian, Shanghai (CN); Song Li, Shanghai (CN)

(73) Assignee: IMMUNEONCO BIOPHARMACEUTICALS (SHANGHAI) INC., Shanghai (CN)

( * ) Notice: Subject to any disclaimer, the term of this patent is extended or adjusted under 35 U.S.C. 154(b) by 0 days.

(21) Appl. No.: 17/496,051

(22) Filed: Oct. 7, 2021

(65) Prior Publication Data
US 2023/0083670 A1 Mar. 16, 2023

(30) Foreign Application Priority Data
Sep. 15, 2021 (CN) .......................... 202111083819.5

(51) Int. Cl.
| | | |
|---|---|---|
| A61K 39/395 | (2006.01) |
| A61K 38/17 | (2006.01) |
| C07K 16/30 | (2006.01) |
| C07K 16/46 | (2006.01) |
| C07K 16/28 | (2006.01) |
| C12N 15/63 | (2006.01) |
| A61P 35/00 | (2006.01) |
| A61K 39/00 | (2006.01) |

(52) U.S. Cl.
CPC ...... *A61K 39/39558* (2013.01); *A61K 38/177* (2013.01); *A61P 35/00* (2018.01); *C07K 16/2827* (2013.01); *C07K 16/30* (2013.01); *C07K 16/3046* (2013.01); *C07K 16/3061* (2013.01); *C07K 16/468* (2013.01); *C12N 15/63* (2013.01); *A61K 2039/505* (2013.01); *C07K 2317/51* (2013.01); *C07K 2317/515* (2013.01)

(58) Field of Classification Search
CPC ................. C07K 16/30; C07K 16/468; A61K 39/39558; A61K 39/39541
See application file for complete search history.

(56) References Cited

U.S. PATENT DOCUMENTS

| 2004/0213791 | A1* | 10/2004 | Bander | A61K 47/6869 424/155.1 |
| 2007/0059806 | A1* | 3/2007 | Arnon | A61P 11/00 435/5 |
| 2021/0388043 | A1* | 12/2021 | Tian | C12N 15/63 |

FOREIGN PATENT DOCUMENTS

JP  2021500042 A  1/2021

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Burgess et al. (J of Cell Bio. 111:2129-2138, 1990) (Year: 1990).*
Lazar et al. (Molecular and Cellular Biology 8:1247-1252, 1988) (Year: 1988).*
Ju (Proceedings of the National Academy of Sciences, U.S.A., vol. 88, p. 2658-2662, 1991) (Year: 1991).*
Baker (Immunity, vol. 13, p. 475-484, 2000) (Year: 2000).*
Nonaka (Human Molecular Genetics, vol. 18, No. 18, p. 3353-3364, 2009) (Year: 2009).*
Bowie et al. (Science, 247:1306-1310, 1990, p. 1306, col. 2) (Year: 1990).*
Martindale (Nature Genetics, vol. 18, p. 150-154, 1998) (Year: 1998).*
Office action dated Jan. 4, 2022 issued in counterpart Japanese Application No. JP2021-163660.

* cited by examiner

*Primary Examiner* — Michael Allen
(74) *Attorney, Agent, or Firm* — Duane Morris LLP; Thomas J. Kowalski; Deborah L. Lu

(57) ABSTRACT

The present application provides a recombinant fusion protein containing an anti-PD-L1 antibody or an antibody fragment thereof, with each paratope of the anti-PD-L1 antibody or antibody fragment thereof linked via a linker to an extracellular Ig-like domain of a signal-regulatory protein (SIRP) at N-terminus of a heavy chain variable region or a light chain variable region constituting the paratope, wherein the recombinant fusion protein can bind to CD47, PD-L1 and FcR simultaneously. The present application also provides a nucleic acid molecule encoding the recombinant fusion protein, an expression vector containing the nucleic acid molecule, a method for producing the recombinant fusion protein and a method for treating a disease associated with over-expression of CD47 and/or PD-L1 using the recombinant fusion protein.

15 Claims, 8 Drawing Sheets

Specification includes a Sequence Listing.

RECOMBINANT FUSION PROTEINS TARGETING CD47 AND PD-L1, PREPARATION AND USE THEREOF

RELATED APPLICATIONS AND INCORPORATION BY REFERENCE

This application claims priority to Chinese Patent Application No. 202111083819.5 filed on Sep. 15, 2021.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy, is named 55525_00041SL.txt and is 43 kbytes in size.

FIELD OF THE INVENTION

The application relates to a recombinant fusion protein targeting CD47, PD-L1 and/or FcR, preparation and use thereof, especially its use in tumor therapies.

BACKGROUND OF THE INVENTION

Cancer cells have developed several mechanisms to escape from host immune surveillance, including, but not limited to, 1) to highly express membrane PD-L1 and PD-L2 proteins, both of which bind to PD-1s on T cell surfaces, inducing T-cell apoptosis; 2) to promote detachment of MICA/MICB from cancer cell membranes, which bind to NKG2D proteins on natural killer (NK) cell surfaces, blocking MICA/MICB$^+$ cancer cell killing by NK cells; 3) to express on surfaces a high level of CD47s, which bind to the signal regulatory protein alpha (SIRPα) on macrophage surfaces, thereby inducing inhibitory signals that inhibit the phagocytosis of cancer cells by macrophages. It can be seen that the cancer cells are quite "smart" and reproduce quickly depending on their developed evasion mechanisms. Accordingly, development of effective anti-cancer drugs for killing the cancer cells may focus on targeting these mechanisms.

SIRP and CD47

Signal regulatory protein (SIRP) is a trans-membrane glycoprotein, including three family members, SIRPα (CD172a), SIRPβ (CD172b) and SIRPγ (CD172g). All three proteins comprise similar extracellular regions but distinct intracellular domains. The extracellular region contains three immunoglobulin-like domains, one Ig V-set and two Ig C-set domains. The intracellular domain of SIRPα (CD172a) contains two inhibitory signaling regions that can inhibit signal transduction and corresponding cell functions. SIRPβ (CD172b) and SIRPγ (CD172g) have very short intracellular regions without any signal transduction domain. However, SIRPβ (CD172b) may function through an adaptor protein, e.g., DAP12 for signal transduction. SIRPs are mainly expressed on macrophages (Mφ), dendritic cells (DCs) and neurons.

CD47 is a transmembrane glycoprotein belonging to the immunoglobulin superfamily, and is expressed on the surface of all cell types including red blood cells. Ligands for CD47 include integrins, thrombospondin-1 and SIRPs. CD47, by interacting with SIRPα to emit a 'don't eat me' signal, can inhibit phagocytosis by macrophages and thus protects cells, such as blood cells, from being attacked by macrophages.

Studies have shown that many tumor or cancer cells over-express CD47s, which prevent phagocytosis of the cancer cells by macrophages. Cancer cells that over-express CD47 include cells of acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, and pancreatic cancer. It is reported that injection of CD47 specific antibody that blocks the binding of CD47 to SIRPα can significantly inhibit tumor growth in tumor-bearing mice. Tumor or cancer cells were eliminated completely when the same antibody was injected into the mice carrying human leukemia cells (Theocharides APA, et al., 2012).

PD-L1 and PD-1

PD-L1, also known as programmed death-ligand 1 or CD274, is a transmembrane protein that plays a major role in suppressing the immune system during some particular events such as tissue allografts, autoimmune disease and cancer development. In cancers, loss of feedback restriction between transcription factors like STAT3 and NF-κB can lead to increased local PD-L1 expression, which could limit the effectiveness of systemic treatment with agents targeting PD-L1 (Vlahopoulos SA, 2017). An analysis of 196 tumor specimens from patients with renal cell carcinoma found that high tumor expression of PD-L1 was associated with increased tumor aggressiveness and a 4.5-fold increased risk of death (Thompson RH et al., 2004).

PD-1 is a cell surface receptor of about 268 amino acids. When bound with PD-L1 or PD-L2, it down-regulates the immune system and promotes self-tolerance by suppressing T cell inflammatory activity. The inhibitory effect of PD-1 on immune system prevents autoimmune diseases but also prevent the immune system from killing cancer cells. An anti-PD-1 antibody, BMS-936558, produced objective responses in approximately one in five to one in four patients with non-small-cell lung cancer, melanoma, or renal-cell cancer (Suzanne L. Topalian et al., 2012).

Fc and FcR

The fragment crystallizable region (Fc region) is the tail region of an antibody and is the domain that determines the effector function of the antibody, that is, how it engages with specific cell receptors or other defense proteins.

An Fc receptor (FcR) is a protein found on the surface of certain cells, including B lymphocytes, follicular dendritic cells, natural killer cells, macrophages, neutrophils, eosinophils, basophils, and mast cells. These cells contribute to the protective functions of the immune system.

An Fc region may interact with Fc receptors and some proteins of the complement system, which activates the immune system.

Therapeutic Bi-Specific or Multi-Specific Fusion Proteins/Antibodies

Antibodies targeting a single antigen have been found to have limited therapeutic efficacy. For example, the overall response rate of an approved anti-PD-L1 antibody, Avelumab (BAVENCIO), is only 33%. Bi- or tri-specific fusion proteins have been developed in recent years, and shown promising effects in pre-clinical and clinical tests.

Although attaching additional binding moieties to conventional antibodies seems conceptually straightforward, such modification significantly alters antibody structures and may compromise one another's affinity and/or efficacy (Wang S et al., 2021). In order to optimize in vivo efficacy and pharmaceutical properties, elaborate design and engineering should be given to choice of main and appended binding moieties (sequences), balanced affinities for targets, sites of attachment (N- or C-termini, heavy or light chains), structural stability, linker lengths and sequences (Shim H. 2020).

U.S. Pat. No. 10,800,821 B2 discloses a recombinant bi-functional fusion protein of about 90 kDa, targeting both CD47 and FcR, which was used to treat Balb/c nude mice carrying HL cells, and an enhanced anti-tumor effect was observed. U.S. Pat. No. 10,973,878 B2 discloses a fusion protein (i.e., IMM2505) that accurately targets CD47, PD-L1 and FcR at the same time and is of a low molecular weight and has a long half-life.

Citation or identification of any document in this application is not an admission that such document is available as prior art to the present disclosure.

SUMMARY OF THE INVENTION

The present inventors have designed and prepared a recombinant fusion protein that has a similar structure to IMM2505 but with a novel anti-PD-L1 antibody, and this novel fusion protein has shown superior anti-tumor effect to IMM2505.

Specifically, the present application discloses a recombinant fusion protein, comprising an anti-PD-L1 antibody or an antibody fragment thereof specifically binding to PD-L1, and a CD47 binding peptide, wherein the CD47 binding peptide is linked to the anti-PD-L1 antibody or antibody fragment thereof, wherein the anti-PD-L1 antibody or antibody fragment thereof comprises a heavy chain variable region having an amino acid sequence having at least 95% sequence identity to SEQ ID NO: 19, a light chain variable region having an amino acid sequence having at least 95% sequence identity to SEQ ID NO: 20, and a heavy chain constant region that has FcR binding capability and is linked to the C terminus of the heavy chain variable region, wherein the CD47 binding peptide comprises a mutated signal-regulatory protein (SIRP) extracellular domain having an amino acid sequence having at least 95% sequence identity to SEQ ID NO: 2, wherein the recombinant fusion protein can bind to CD47 and PD-L1 simultaneously. The CD47 binding peptide may bind to the N-terminus of the heavy chain variable region or the light chain variable region of the anti-PD-L1 antibody or antibody fragment thereof. The amino acid sequence of SEQ ID NO: 2 may be encoded by the nucleic acid sequence of SEQ ID NO: 1.

In certain embodiments, at least one paratope of the anti-PD-L1 antibody or antibody fragment thereof is linked to the CD47 binding peptide at N-terminus of the heavy chain variable region or the light chain variable region constituting the paratope. In certain embodiments, each paratope of the anti-PD-L1 antibody or antibody fragment thereof is linked to the CD47 binding peptide at N-terminus of the heavy chain variable region or the light chain variable region constituting the paratope. In certain embodiments, each paratope of the anti-PD-L1 antibody or antibody fragment thereof is linked to the CD47 binding peptide at N-terminus of the heavy chain variable region constituting the paratope. In certain embodiments, each paratope of the anti-PD-L1 antibody or antibody fragment thereof is linked to the CD47 binding peptide at N-terminus of the light chain variable region constituting the paratope.

The heavy chain constant region having FcR binding capability may be a naturally occurring or engineered human IgG1, IgG2, IgG3 or IgG4 heavy chain constant region, or a functional fragment thereof. In certain embodiments, the heavy chain constant region having FcR binding capability is a human IgG1 heavy chain constant region, or a functional fragment thereof. In certain embodiments, the heavy chain constant region having FcR binding capability has the amino acid sequence of SEQ ID NO: 21.

The anti-PD-L1 antibody or antibody fragment thereof may comprise a light chain constant region, e.g., human kappa light chain constant region, or a functional fragment thereof, linked to the C terminus of the light chain variable region.

In certain embodiments, the anti-PD-L1 antibody or antibody fragment thereof may comprise a heavy chain variable region-heavy chain constant region fragment having an amino acid sequence having at least 80%, 85%, 90%, 91%, 92%, 93%, 94%, 95%, 96%, 97%, 98% or 99% sequence identity to SEQ ID NO: 6, and a light chain variable region having an amino acid sequence having at least 80%, 85%, 90%, 91%, 92%, 93%, 94%, 95%, 96%, 97%, 98%, or 99% sequence identity to SEQ ID NO: 20. In certain embodiments, the anti-PD-L1 antibody or antibody fragment thereof may comprise a heavy chain variable region-heavy chain constant region fragment having an amino acid sequence having at least 80%, 85%, 90%, 91%, 92%, 93%, 94%, 95%, 96%, 97%, 98%, or 99% sequence identity to SEQ ID NO: 6, and a light chain variable region-light chain constant region fragment having an amino acid sequence having at least 80%, 85%, 90%, 91%, 92%, 93%, 94%, 95%, 96%, 97%, 98%, or 99% sequence identity to SEQ ID NO: 8. In certain embodiments, the anti-PD-L1 antibody or antibody fragment thereof may comprise a heavy chain variable region-heavy chain constant region fragment having the amino acid sequence of SEQ ID NO: 6, and a light chain variable region having the amino acid sequence of SEQ ID NO: 20. In certain embodiments, the anti-PD-L1 antibody or antibody fragment thereof may comprise a heavy chain variable region-heavy chain constant region fragment having the amino acid sequence of SEQ ID NO: 6, and a light chain variable region-light chain constant region fragment having the amino acid sequence of SEQ ID NO: 8. The amino acid sequences of SEQ ID NOs: 6 and 8 may be encoded by the nucleic acid sequences of SEQ ID NOs: 5 and 7, respectively.

The anti-PD-L1 antibody or antibody fragment thereof may be linked to the CD47 binding peptide via a linker. The linker may be a peptide of 5-30, 10-30, 10-20 or 15 amino acid residues. The linker may be—(Gly-Gly-Gly-Gly-Ser)$_2$—(SEQ ID NO: 17),—(Gly-Gly-Gly-Gly-Ser)$_3$—(SEQ ID NO: 4), or—(Gly-Gly-Gly-Gly-Ser)$_4$—(SEQ ID NO: 18). In certain embodiments, the linker is—(Gly-Gly-Gly-Gly-Ser)$_3$—(SEQ ID NO: 4). The amino acid sequence of SEQ ID NO: 4 may be encoded by the nucleic acid sequence of SEQ ID NO: 3.

In certain embodiments, the recombinant fusion protein comprise a CD47 binding peptide-linker-anti-PD-L1 heavy chain variable region-heavy chain constant region fragment having an amino acid sequence having at least having at least 80%, 85%, 90%, 91%, 92%, 93%, 94%, 95%, 96%, 97%, 98% or 99% sequence identity to SEQ ID NO: 10, and an anti-PD-L1 light chain variable region-light chain constant region fragment having an amino acid sequence having at least having at least 80%, 85%, 90%, 91%, 92%, 93%, 94%, 95%, 96%, 97%, 98% or 99% sequence identity to SEQ ID NO: 8. In certain embodiments, the recombinant fusion protein comprise a CD47 binding peptide-linker-anti-PD-L1 heavy chain variable region-heavy chain constant region fragment having an amino acid sequence having at least having at least 80%, 85%, 90%, 91%, 92%, 93%, 94%, 95%, 96%, 97%, 98% or 99% sequence identity to SEQ ID NO: 10, and an anti-PD-L1 light chain variable region having an amino acid sequence having at least having at least 80%, 85%, 90%, 91%, 92%, 93%, 94%, 95%, 96%, 97%, 98% or 99% sequence identity to SEQ ID NO: 20. In certain embodiments, the recombinant fusion protein comprise a CD47 binding peptide-linker-anti-PD-L1 heavy chain variable region-heavy chain constant region fragment having the amino acid sequence of SEQ ID NO: 10, and an anti-PD-L1 light chain variable region-light chain constant region fragment having the amino acid sequence of SEQ ID NO: 8. In certain embodiments, the recombinant fusion protein comprise a CD47 binding peptide-linker-anti-PD-L1 heavy chain variable region-heavy chain constant region fragment having the amino acid sequence of SEQ ID NO: 10, and an anti-PD-L1 light chain variable region having the amino acid sequence of SEQ ID NO: 20. The amino acid sequences of SEQ ID NOs: 8 and 10 may be encoded by the nucleic acid sequences of SEQ ID NOs: 7 and 9, respectively.

In certain embodiments, the recombinant fusion protein comprises an anti-PD-L1 heavy chain variable region-heavy chain constant region fragment having an amino acid sequence having at least 80%, 85%, 90%, 91%, 92%, 93%, 94%, 95%, 96%, 97%, 98% or 99% sequence identity to SEQ ID NO: 6, and a CD47 binding peptide-linker-anti-PD-L1 light chain variable region-light chain constant region fragment having an amino acid sequence having at least 80%, 85%, 90%, 91%, 92%, 93%, 94%, 95%, 96%, 97%, 98% or 99% sequence identity to SEQ ID NO: 16. In certain embodiments, the recombinant fusion protein comprises an anti-PD-L1 heavy chain variable region-heavy chain constant region fragment having the amino acid sequence of SEQ ID NO: 6, and a CD47 binding peptide-linker-anti-PD-L1 light chain variable region-light chain constant region fragment having the amino acid sequence of SEQ ID NO: 16. The amino acid sequences of SEQ ID NOs: 6 and 16 may be encoded by the nucleic acid sequences of SEQ ID NOs: 5 and 15, respectively.

The present application also provides a nucleic acid molecule encoding the recombinant fusion protein of the disclosure, as well as an expression vector comprising such a nucleic acid molecule and a host cell comprising such an expression vector. A method for preparing the recombinant fusion protein using the host cell of the disclosure is provided, comprising steps of (i) expressing the recombinant fusion protein in the host cell, and (ii) isolating the recombinant fusion protein from the host cell or its cell culture.

The application further provides a pharmaceutical composition which may comprise the recombinant fusion protein, nucleic acid molecule, expression vector or host cell of the disclosure, and at least one pharmaceutically acceptable excipient. In certain embodiments, the pharmaceutical composition comprises at least one pharmaceutically acceptable adjuvant.

The recombinant fusion protein or pharmaceutical composition of the disclosure may be used in treatment of, or in preparation of a medicament for treating a disease associated with over-expression of CD47 and/or PD-L1.

In one aspect, the present application provides a method for treating or alleviating a disease associated with over-expression of CD47 and/or PD-L1 in a subject in need thereof, comprising administering to the subject a therapeutically effective amount of the pharmaceutical composition of the disclosure.

The disease may be acute myelocytic leukemia (AML), chronic myelocytic leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer, or renal cell carcinoma.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the application not to encompass within the application any previously known product, process of making the product, or method of using the product such that Applicants reserve the right and hereby disclose a disclaimer of any previously known product, process, or method. It is further noted that the application does not intend to encompass within the scope of the application any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the application to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the application.

DESCRIPTION OF THE DRAWINGS

The following detailed description, given by way of example, but not intended to limit the application solely to the specific embodiments described, may best be understood in conjunction with the accompanying drawings.

DETAILED DESCRIPTION OF THE APPLICATION

Figure 1A:
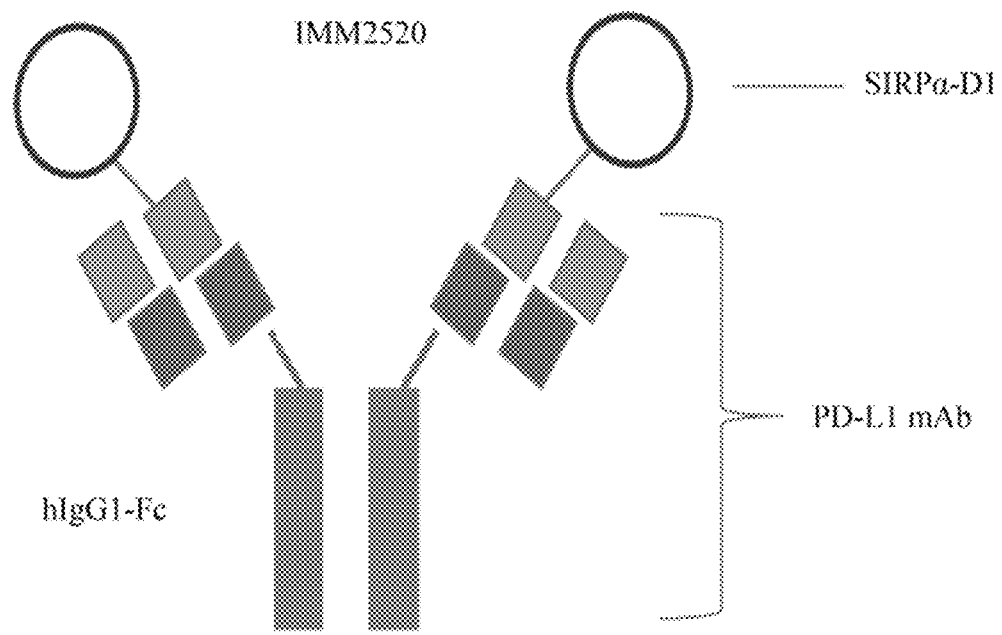
FIGS. 1A and 1B are schematic diagrams of structures of the recombinant fusion proteins, IMM2520 and IMM2521, of the present application. The top circular domain represents mutated extracellular domain 1 of SIRP alpha protein (SIRPαD1), which is linked to the N terminus of the heavy chain (A) or the light chain (B) of an anti-PD-L1 antibody via a peptide linker. The mutated SIRPαD1 has the nucleic acid and amino acid sequences set forth in SEQ ID NO: 1 and SEQ ID NO: 2, respectively. The linker having the amino acid sequence of SEQ ID NO: 4 may be encoded by the nucleic acid sequence of SEQ ID NO: 3. The heavy chain of the anti-PD-L1 antibody has the nucleic acid and amino acid sequences set forth in SEQ ID NO: 5 and SEQ ID NO: 6, respectively. The light chain of the anti-PD-L1 antibody has the nucleic acid and amino acid sequences set forth in SEQ ID NO: 7 and SEQ ID NO: 8, respectively.

There are principally three different approaches to targeting two or more pharmacological targets of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems can reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single compound. The design and validation of such multifunctional molecules are more complex and require substantial investigation into the optimal ratio of target activities in the molecule, but the unified pharmacokinetics may yield matched pharmacodynamic activities at the molecular targets. Multifunctional molecules may also be amenable to fixed dose combination with other drugs thereby combining three or even four pharmacologies in a single pill to produce further increments in efficacy.

Through diligent experimentation, the present inventor has invented a novel recombinant multi-functional fusion protein, which can attack tumors, via three mechanisms of actions, one to release the check or inhibition on T cells by PD-1-mediated inhibitory signals, one to release the check on macrophages by SIRP-mediated inhibitory signals, another to stimulate cancer cell killings by NK cells and/or macrophages.

The recombinant fusion protein of the present application comprises an anti-PD-L1 antibody or an antibody fragment thereof, with at least one paratope of the anti-PD-L1 antibody or antibody fragment linked via a linker to an extracellular Ig-like domain of a signal-regulatory protein (SIRP) at the N-terminus of a heavy chain variable region or a light chain variable region constituting the paratope. The recombinant protein can bind to CD47, PD-L1 and FcR simultaneously, i) blocking the interaction of PD-L1 on cancer cells with PD-1 on T cells and thus releasing the check on T cells by PD-1-mediated inhibitory signals; ii) blocking the interaction of CD47 on cancer cells with SIRPs on macrophages and thus releasing the check on macrophages by SIRP-mediated inhibitory signals; and iii) binding Fc portion of the antibody to FcRs on NK cells or macrophages to stimulate cancer cell killings by NK cells or macrophages. In an embodiment, one paratope of the anti-PD-L1 antibody is linked via a linker to an extracellular Ig-like domain of a signal-regulatory protein (SIRP) at the N-terminus of a heavy chain variable region or a light chain variable region constituting the paratope. In another embodiment, each paratope of the anti-PD-L1 antibody is linked via a linker to an extracellular Ig-like domain of a signal-regulatory protein (SIRP) at the N-terminus of a heavy chain variable region or a light chain variable region constituting the paratope. In one embodiment, each paratope of the anti-PD-L1 antibody is linked via a linker to an extracellular Ig-like domain of a signal-regulatory protein (SIRP) at the N-terminus of a heavy chain variable region constituting the paratope. In one embodiment, each paratope of the anti-PD-L1 antibody is linked via a linker to an extracellular Ig-like domain of a signal-regulatory protein (SIRP) at the N-terminus of a light chain variable region constituting the paratope. The recombinant fusion protein of the present application is small in size (150-180 kDa) and has a long half-life of 5-10 days.

The three main components contained in the fusion protein of the present application are the extracellular Ig-like domain of a signal-regulatory protein (SIRP), the linker, and the anti-PD-L1 antibody. A person of ordinary skills in the art will recognize that there are many design choices for selecting the above three components. Preferably, human-derived sequence is used in human cancer therapies, as the strong immunogenicity of the proteins or peptides from non-human animals may lead to allergy and other adverse effects. However, other animal proteins or peptides, humanized if appropriate, may also be used in the present application based on different application purposes.

Any extracellular Ig-like domain of any SIPR (SIRPα, SIRPβ, and SIRPγ) capable of binding with CD47 may be selected for construction of the fusion protein. In one embodiment, the signal-regulatory protein in the recombinant fusion protein is SIRPα, and the extracellular Ig-like domain of the signal-regulatory protein is the first extracellular Ig-like domain of SIRPα (SIRPαD1). In certain embodiments, SIRPαD1 is a SIRPαD1 mutant that contains an N→A mutation at position 80 of SEQ ID NO: 2 to remove a glycosylation site.

In one embodiment, the recombinant fusion protein comprises SIRPαD1 having the nucleic acid and amino acid sequences set forth in SEQ ID NOs: 1 and 2, respectively. In another embodiment, the SIRPαD1 may comprise an amino acid sequence having at least 80%, 85%, 90%, 95%, 98% or 99% sequence identity to SEQ ID NO: 2, wherein the SIRPαD1 can bind to CD47 on the cell surface of cancer/tumor cells and block the interaction of CD47 with SIRPs on the cell surfaces of macrophages.

Linkers serve primarily as a spacer between the extracellular Ig-like domain of SIRP and the N-terminus of the heavy chain or light chain of an anti-PD-L1 antibody. The linker may be made up of amino acids linked together by peptide bonds, preferably from 5 to 30 amino acids, from 10 to 30 amino acids, from 10 to 20 amino acids, or 15 amino acids, linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, poly(Gly-Ala), and polyalanines. One exemplary suitable linker as shown in the Examples below is (Gly-Ser), such as—(Gly-Gly-Gly-Gly-Ser)$_3$—(SEQ ID NO: 4).

Linkers may also be non-peptide linkers. For example, alkyl linkers such as—NH-,-(CH$_2$)s-C(O)-, wherein s=2-20 can be used. These alkyl linkers may further be substituted by any non-sterically hindering group such as lower alkyl (e.g., $C_{1-4}$) lower acyl, halogen (e.g., CI, Br), CN, NH$_2$, phenyl, etc.

In some embodiments, the anti-PD-L1 antibody is an isolated monoclonal antibody comprising two heavy chains each having an amino acid sequence of SEQ ID NO: 6, and two light chains each having an amino acid sequence of SEQ ID NO: 8, which two may be encoded by nucleic acid sequences of SEQ ID NOs: 5 and 7, respectively. The Fab portion (or paratope) of the anti-PD-L1 antibody can bind to PD-L1 on the cell surfaces of cancer/tumor cells to block the interaction of PD-L1 with PD-1 on the cell surfaces of T cells and thus release the check on T cells by PD-1-mediated inhibitory signals, while the Fc portion of the anti-PD-L1 antibody can bind to FcRs on the cell surfaces of NK cells or macrophages to stimulate cancer cell killings by the NK cells or macrophages. In some embodiments, the heavy chain may comprise an amino acid sequence having at least 80%, 85%, 90%, 95%, 98% or 99% sequence identity to SEQ ID NO: 6, wherein the anti-PD-L1 antibody is able to bind to PD-L1 and block the interaction of PD-L1 with PD-1 on the cell surfaces of T cells, and is also able to bind to FcRs on the cell surfaces of NK cells or macrophages and thus activate the NK cells or macrophages for killing the cancer cells. In some embodiments, the light chain may comprise an amino acid sequence having at least 80%, 85%, 90%, 95%, 98% or 99% sequence identity to SEQ ID NO: 8, wherein the anti-PD-L1 antibody is able to bind to PD-L1 and block the interaction of PD-L1 with PD-1 on the cell surfaces of T cells.

The term "antibody" as referred to herein includes whole antibodies of e.g., IgG, IgA, IgD, IgE and IgM, and any antigen binding fragment (i.e., "antigen-binding portion") or single chains thereof Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody fragment" herein refers to a portion or fragment of an anti-PD-L1 antibody of the disclosure that retains the ability to specifically bind to a PD-L1, and optionally the ability to bind Fc receptors.

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega, T-coffee, Kalign and MAFFT. When using such softwares, the default parameters, e.g. for gap penalty and extension penalty, are preferably used.

Also, the present application provides a polynucleotide molecule encoding the recombinant fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present application provides host cells comprising the above expression vectors. The host cells may be transformed or transfected with the expression vectors. Suitable host cells include *Escherichia coli*, yeasts and other eukaryotes. Preferably, *Escherichia coli*, yeast or mammalian cell lines (such as COS or CHO) are used.

In another aspect, the present disclosure provides a pharmaceutical composition comprising the fusion protein of the present application formulated together with a pharmaceutically acceptable . The composition may optionally contain one or more additional pharmaceutically active ingredients, such as another antibody or a drug. The pharmaceutical compositions of the application also can be administered in a combination therapy with, for example, another immune-stimulatory agent, anti-cancer agent, an anti-viral agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present application, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the application can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the fusion protein can be administered as a sustained release formulation, in which case less frequent administration is required.

For administration of the fusion protein, the dosage ranges from about 0.0001 to 100 mg/kg of the host body weight. An exemplary treatment regime entails administration twice per week.

A "therapeutically effective dosage" of a fusion protein of the application preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a fusion protein of the present application can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the fusion protein of the application can be formulated to ensure proper distribution in vivo. For example, to ensure that the therapeutic fusion proteins of the application cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331.

A gene therapy in vivo is also envisioned wherein a nucleic acid molecule encoding the recombinant fusion protein of the present application, or a derivative thereof is introduced directly into the subject. For example, a nucleic acid sequence encoding a recombinant fusion protein of the present application is introduced into target cells via local injection of a nucleic acid construct with or without an appropriate delivery vector, such as an adeno- associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present application is to provide a method for preparing the above recombinant fusion protein and the pharmaceutical composition comprising the same. In one embodiment, the method comprises (1) providing a protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present application is to provide a method of treating cancer using the pharmaceutical composition of the present application, comprising administrating an effective amount of the aforementioned pharmaceutical composition to the patients or subjects in need thereof. In one embodiment, the pharmaceutical composition is used to treat CD47and/or PD-L1-overexpressing tumors or cancers, including but not limited to acute myeloid leukemia (AML), chronic myeloid leukemia (CML), acute lymphoblastic leukemia (ALL), non-hodgkins lymphoma (NHL), multiple myeloma (MM), bladder cancer, ovarian cancer, prostate cancer, lung cancer, colon cancer, breast cancer, pancreatic cancer and renal cancer.

In one embodiment, the diseases related to over-expressions of CD47 and/or PD-L1 include, but are not limited to, Crohn's disease, allergic asthma, and rheumatoid arthritis.

The present application is now further described with the non-limiting examples below.

EXAMPLES

The recombinant proteins described herein and below will be introduced first.

IMM2515 is a monoclonal anti-PD-L1 antibody that comprises two heavy chains each having the amino acid sequence of SEQ ID NO: 6, and two light chains each having the amino acid sequence of SEQ ID NO: 8, which two may be encoded by nucleic acid sequences of SEQ ID NOs: 5 and 7, respectively.

IMM01, as described in US 2021/0024598 A1, comprises two mutated SIRPαD1s (SEQ ID NO: 2) linked to an Fc dimer fragment, whose monomer has the nucleic acid and amino acid sequences of SEQ ID NO: 11 and SEQ ID NO: 12, respectively.

IMM2520 is a recombinant fusion protein, containing two mutated SIRPαD1s each linked via a GS-linker, to IMM2515 at the N-terminus of each heavy chain, wherein the mutated SIRPαD1 has an nucleic acid sequence and amino acid sequence of SEQ ID NO: 1 and SEQ ID NO: 2, respectively, and the linker having an amino acid sequence of SEQ ID NO: 4 can be encoded by the nucleic acid sequence of SEQ ID NO: 3.

IMM2521 is a recombinant fusion protein, containing two mutated SIRPαD1s each linked via a GS-linker, to IMM2515 at the N-terminus of each light chain, wherein the mutated SIRPαD1 has an nucleic acid sequence and amino acid sequence of SEQ ID NO: 1 and SEQ ID NO: 2, respectively, and the linker having an amino acid sequence of SEQ ID NO: 4 can be encoded by the nucleic acid sequence of SEQ ID NO: 3.

IMM2505 is a fusion protein disclosed in U.S. Pat. No. 10,973,878 B2 that shares a similar overall design with IMM2520 and IMM2521, comprising the mutated SIRPαD1 (SEQ ID NO: 2) and a different anti-PD-L1 antibody.

Example 1. Construction of vectors expressing IMM2520 and IMM2521

Figure 1B:
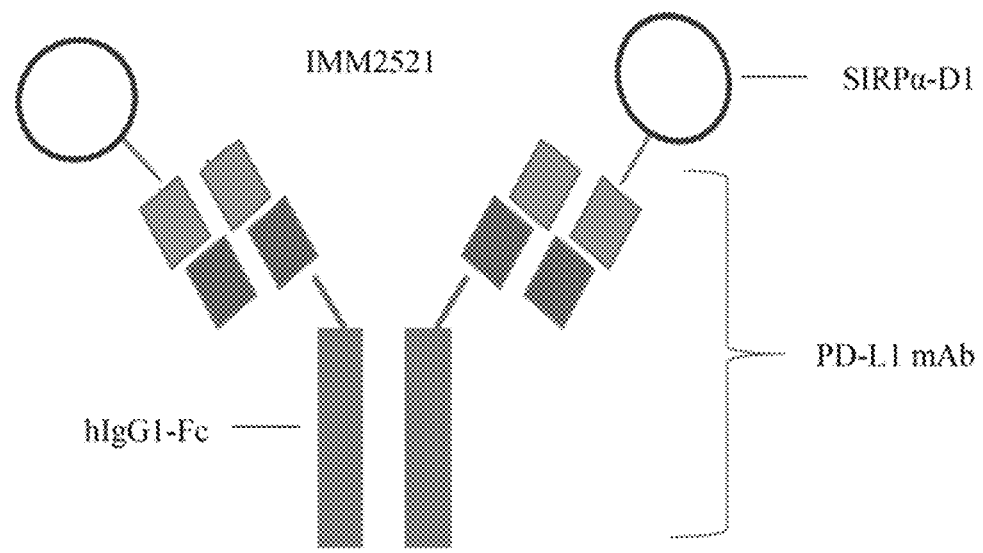
Figure 2:
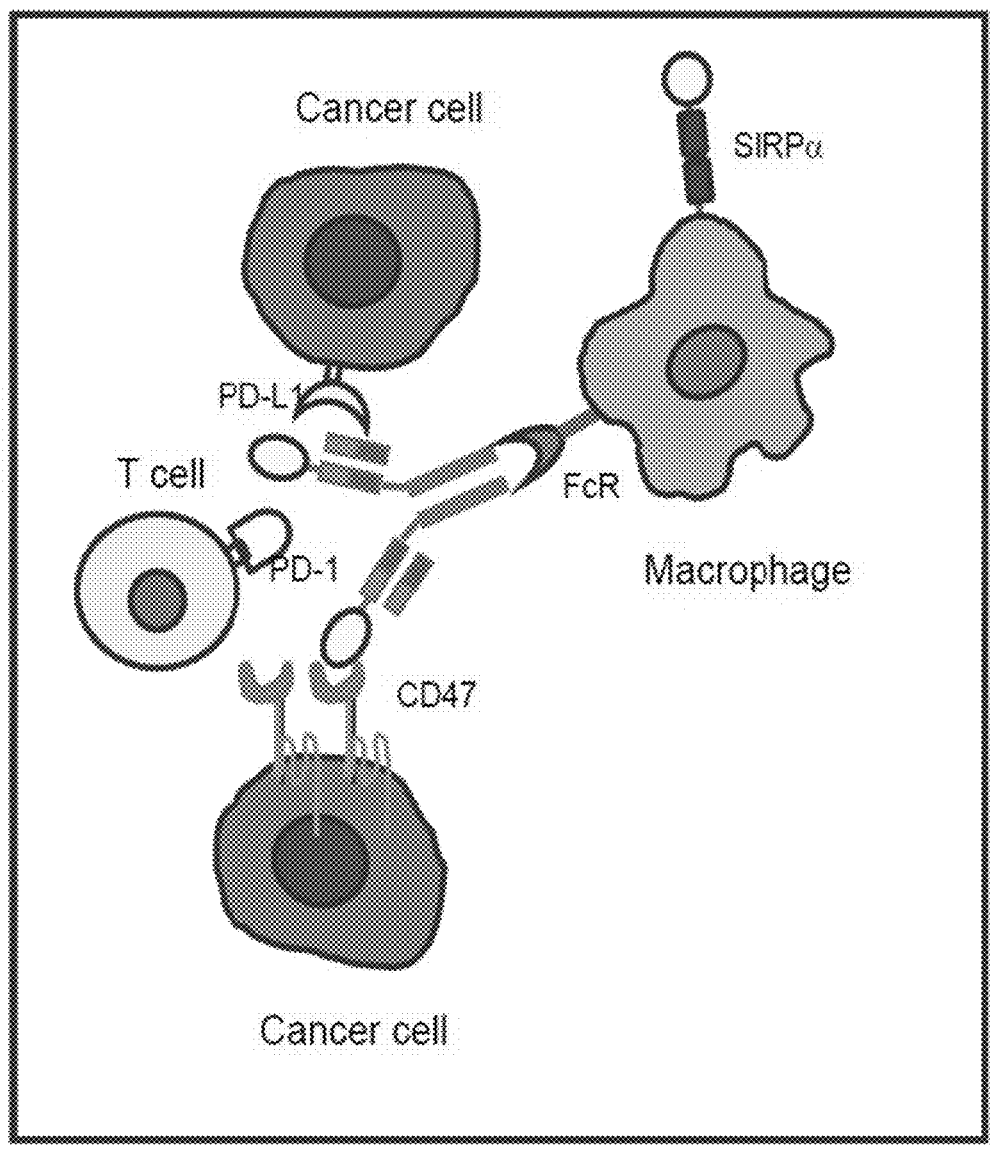
FIG. 2 is a schematic diagram showing action mechanism of the recombinant fusion protein of the present application.

The structures of IMM2520 and IMM2521 were shown in FIGS. 1A and 1B. Full length coding sequences of the recombinant fusion proteins IMM2520 and IMM2521 were designed artificially.

Specifically, for the SIRPαD1-linker-anti-PD-L1 heavy chain in IMM2520, the coding sequence of the mutated SIRPαD1 (SEQ ID NO: 1) was linked through a GS-linker coding sequence (SEQ ID NO: 3) to the 5' end of the anti-PD-L1 heavy chain coding sequence of IMM2515 (SEQ ID NO:5); 57 nucleotides encoding the signal peptide of mouse IgG1 heavy chain (SEQ ID NO: 13) were added to the 5' end of mutated SIRPαD1-coding sequence, and a Kozak sequence (SEQ ID NO: 14) was added to the 5' end of the signal peptide sequence. Lastly, HindIII and NheI restriction sites were added to the 5' and 3' ends of the resulting sequence, respectively. For the anti-PD-L1 light chain in IMM2520, the same signal peptide sequence as well as the Kozak sequence was added to the 5' end of the anti-PD-L1 light chain coding sequence (SEQ ID NO: 7), and the HindIII and the XbaI restriction sites were added to the 5' and 3' ends of the resulting sequence, respectively.

For the SIRPαD1-linker-anti-PD-L1 light chain in IMM2521, the coding sequence of the mutated SIRPαD1 (SEQ ID NO: 1) was linked through a GS-linker coding sequence (SEQ ID NO: 3) to the 5' end of the anti-PD-L1 light chain coding sequence of IMM2515 (SEQ ID NO: 7). For the anti-PD-L1 heavy chain in IMM2521, the same signal peptide sequence as well as the Kozak sequence was added to the 5' end of the anti-PD-L1 heavy chain coding sequence (SEQ ID NO: 5).

The resulting sequences were synthesized by Genscript and subcloned, respectively, into the pMac-H and pMac-L vectors.

Example 2. Protein Expression and Purification

To manufacture the recombinant proteins IMM2520 and IMM2521, the expression vectors were electroporated into Chinese Hamster Ovary (CHO) cells (ATCC, Cat# CCL-61) which were subjected to several rounds of pressure selection of neomycin. The selected stable cells were adapted to a serum-free Balan CD CHO Growth A medium (Irvine Scientific, Cat#94120). For protein expression, cells were seeded in a 3 liter bioreactor and cultured in a fed-batch process. When the cell viability dropped to ~80%, the cell culture supernatants were harvested from the bioreactor and subjected to protein purification by affinity chromatography. The purity of recombinant proteins was above 95%, and the content of endotoxin was below 0.5 U/g.

Example 3. IMM2520 and IMM2521 bound to PD-L1 and CD47

CHO-PD-L1 cells (over-expressing PD-L1, in house made) or Jurkat cells (naturally expressing CD47) were incubated at 4° C. for 1 hour with serially diluted IMM2520, IMM2521 and control agents, respectively. Cells were washed with cold PBS twice, and then incubated with FITC-conjugated secondary antibody against human IgG-Fc (Cat#F9512, Sigma) for 45 min. Cells were washed twice and re-suspended in 200 ml PBS. Then, the cells were subject to FACS analysis using a flow cytometer (Merck Millipore, Guava® easyCyte 5HT).

Figure 3:
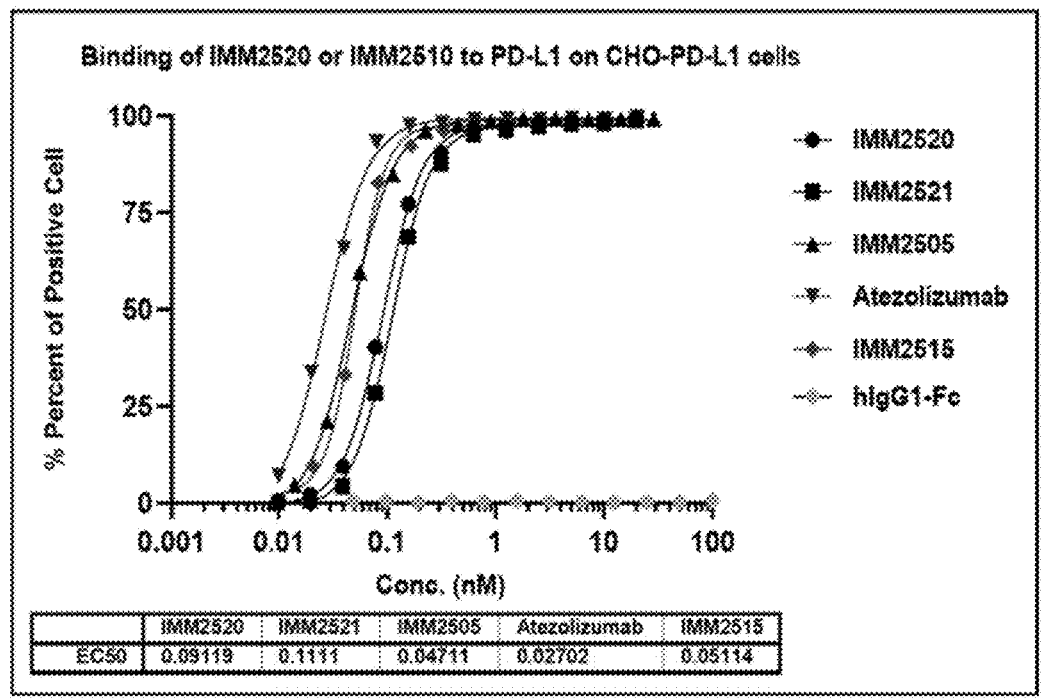
FIG. 3 shows the binding activity of IMM2520 and IMM2521 to PD-L1 on CHO cells expressing human PD-L1 (CHO-PDL1). IMM2505 is a fusion protein described in U.S. Pat. No. 10,973,878 B2 that shares similar overall design with IMM2520 and IMM2521 and comprises the mutated SIRPαD1 (SEQ ID NO: 2) and a different anti-PD-L1 antibody. IMM2515 is an anti-PD-L1 antibody that constitutes IMM2520 and IMM2521 and comprises the heavy chain of SEQ ID NO: 6 and the light chain of SEQ ID NO: 8. Atezolizumab is a commercially available anti-PD-L1 antibody, and hIgG1-Fc was used as the negative control.
Figure 4:
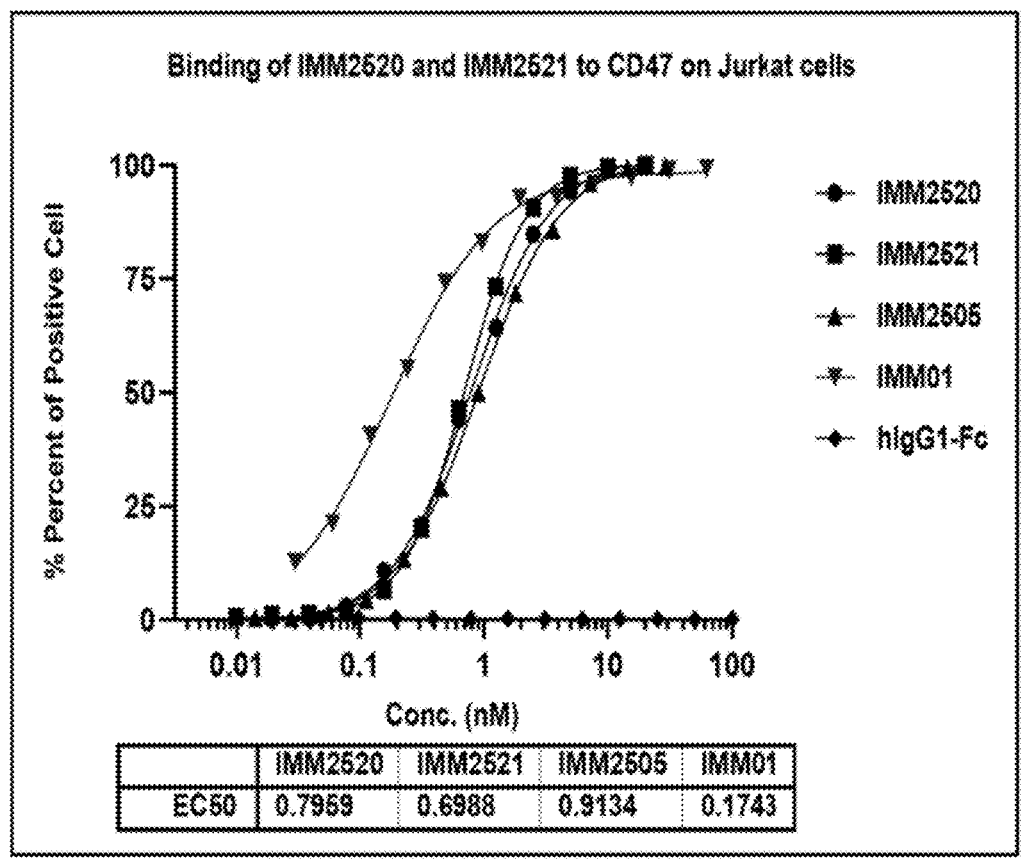
FIG. 4 shows the binding activity of IMM2520 and IMM2521 to CD47 on Jurkat cells. IMM2505 is a fusion protein described in U.S. Pat. No. 10,973,878 B2 that shares similar overall design with IMM2520 and IMM2521 and comprises the mutated SIRPαD1 (SEQ ID NO: 2) and a different anti-PD-L1 antibody. IMM01 was described in US 2021/0024598 A1 and comprises two mutated SIRPαD1s (SEQ ID NO: 2) linked to an Fc dimer fragment, whose monomer has the nucleic acid and amino acid sequences of SEQ ID NO: 11 and SEQ ID NO: 12, respectively. The hIgG1-Fc was used as the negative control.

IMM2520 bound to PD-L1 on CHO cells with an $EC_{50}$ value of 0.09 nM (FIG. 3), and to CD47 on Jurkat cells with an $EC_{50}$ value of 0.80 nM (FIG. 4), slightly inferior to the traditional single antigen targeting proteins. IMM2521 bound to PD-L1 on CHO cells with an $EC_{50}$ value of 0.11 nM (FIG. 3), and to CD47 on Jurkat cells with an $EC_{50}$ value of 0.70 nM (FIG. 4), slightly inferior to the traditional single antigen targeting proteins.

Example 4. IMM2520 and IMM2521 blocked PD-L1-PD-1 Interaction

Biotin-hPD1-mFc proteins (SEQ ID NO: 22), 1 μg/ml, were mixed with serially diluted IMM2520, IMM2521, IMM2515 and hIgG1-Fc, respectively, and the mixtures were then added to a 96-well plate containing $CD47^+$ or $CD47^-$ CHO-PD-L1 cells. Cells were incubated at 4° C. for 45 minutes, washed with PBS, and then further incubated at 4° C. for another 45 minutes with PE-conjugated mouse Anti-human CD279 (Cat#557946, BD BioScience). Cells were washed and re-suspended in 200 ml PBS, and then subjected to FACS analysis for hPD1-mFc-PD-L1 binding/interaction.

Figure 5A:
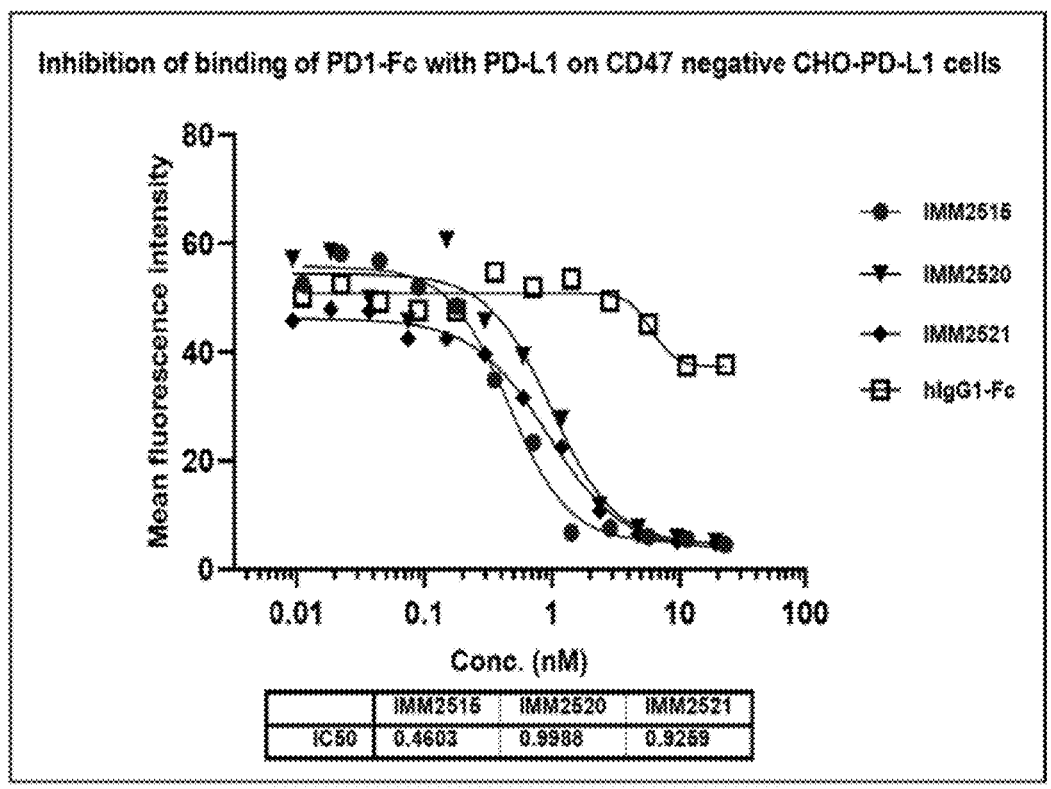
FIGS. 5A and 5B shows the capability of IMM2520 and IMM2521 to block binding of PD-1-Fc to PD-L1 on CD47⁻ CHO-PD-L1 cells (A) or CD47⁺Raji-PD-L1 cells (B). IMM2515 is an anti-PD-L1 antibody that constitutes IMM2520 and IMM2521 and comprises the heavy chain of SEQ ID NO: 6 and the light chain of SEQ ID NO: 8. The hIgG1-Fc was used as the negative control.

As shown in FIG. 5A, IMM2520, IMM2521 and IMM2515 all inhibited interaction of PD1-mFc with $CD47^-$ $PD-L1^+$ cells with $IC_{50}$ values less than 1 nM.

Figure 5B:
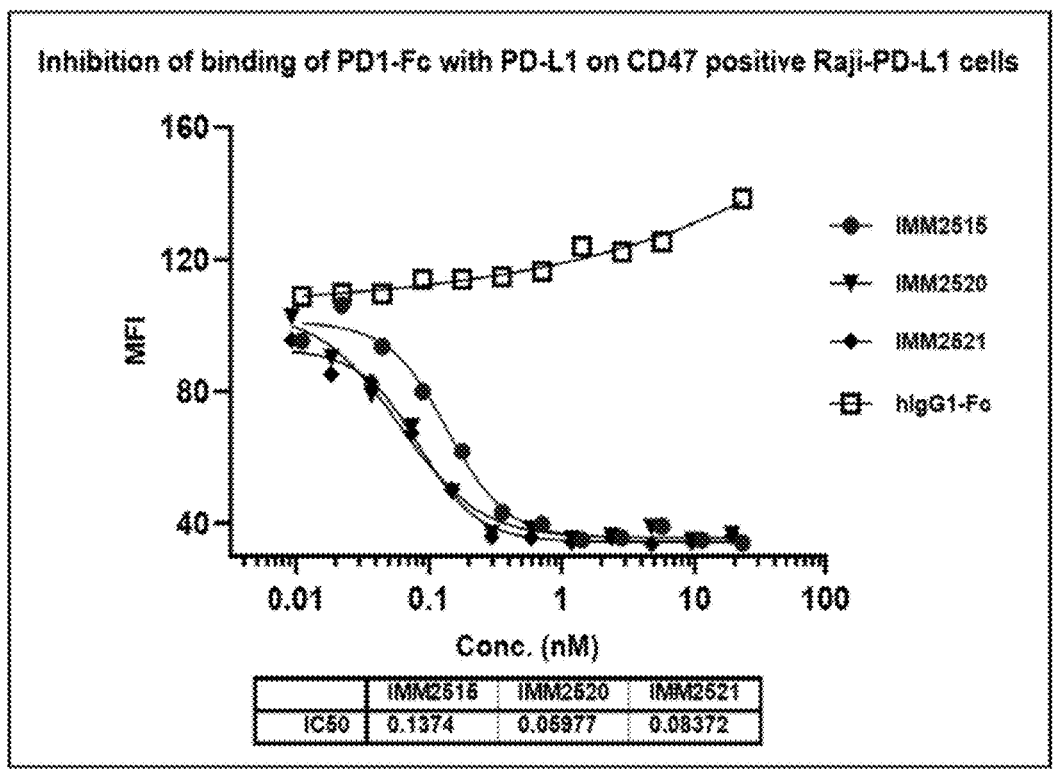

On PD-L1 and CD47 double positive cells (FIG. 5B), the PD-L1×CD47 bispecifics, namely IMM2520 and IMM2521, revealed higher inhibitory activity than the monospecific anti-PD-L1 antibody IMM2515.

Example 5. IMM2520 and IMM2521 blocked CD47-SIRPα Interaction

FITC-conjugated SIRPα-Fc (wild type human SIRPα conjugated with human IgG1 Fc, SEQ ID NO: 23), 80 nM, was mixed with serially diluted IMM2520, IMM2521, IMM01, and hIgG1-Fc, respectively. The mixtures were added to a 96-well plate containing $PD-L1^-$ or $PD-L1^+$ CD47-expressing Raji cells, and the plate was incubated at 4° C. for 45 minutes. Cells were washed with PBS and then subjected to FACS analysis for SIRPα-Fc-CD47 interaction.

Figure 6A:
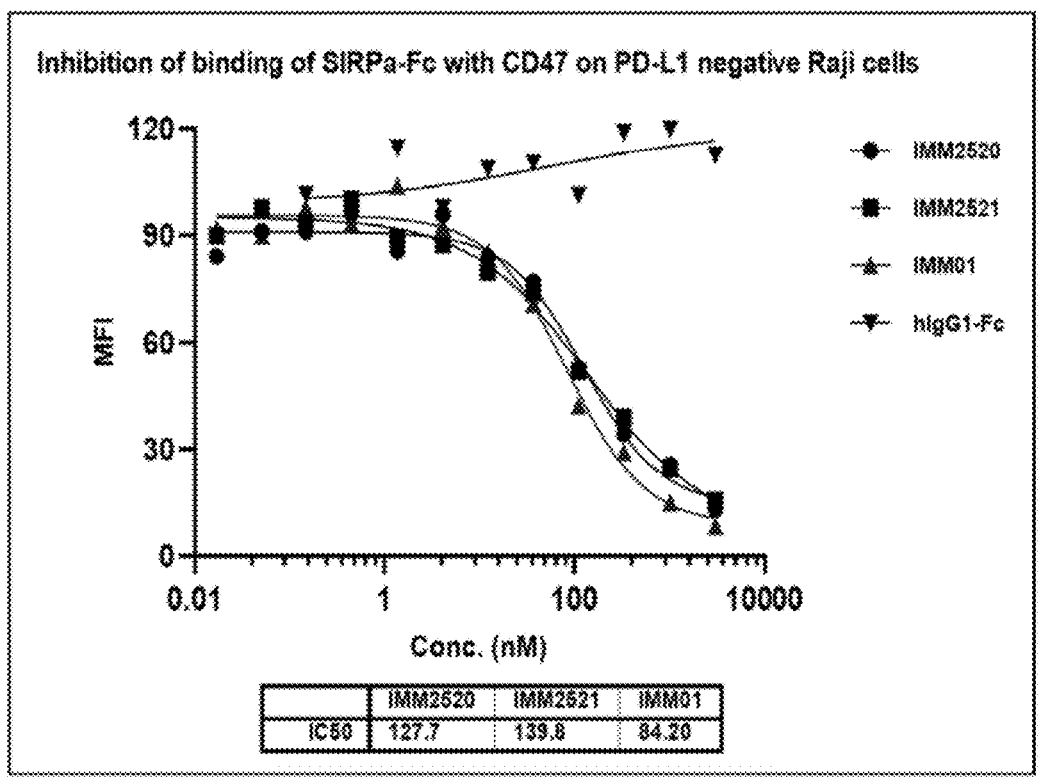
FIGS. 6A and 6B shows the capability of IMM2520 and IMM2521 to block binding of SIRPα-Fc with CD47 on PD-L1⁻Raji cells (A) or Raji-PD-L1 cells (B). IMM01 was described in US 2021/0024598 A1 and comprises two mutated SIRPαD1s (SEQ ID NO: 2) linked to an Fc dimer fragment, whose monomer has the nucleic acid and amino acid sequences of SEQ ID NO: 11 and SEQ ID NO: 12, respectively. The hIgG1-Fc was used as the negative control.

As shown in FIG. 6A, IMM2520 inhibited interaction of SIRPα-Fc with $PD-L1^-$ $CD47^+$ cells with an $IC_{50}$ value of 127.7 nM, while IMM2521 inhibited interaction of SIRPα-Fc with $PD-L1^-CD47^+$ cells with an $IC_{50}$ value of 139.8 nM.

Figure 6B:
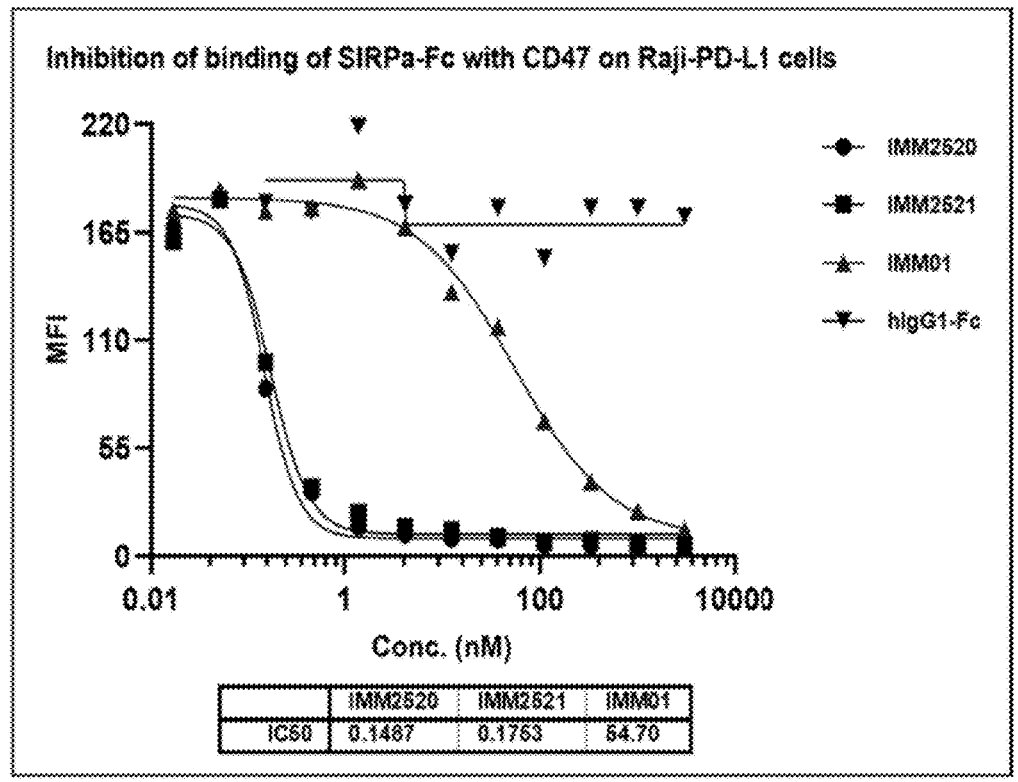

On PD-L1 and CD47 double positive cells (FIG. 6B), the PD-L1×CD47 bispecifics, namely IMM2520 and IMM2521, revealed much higher inhibitory activity than the monospecific IMM01.

Example 6. IMM2520 Induced High Level of Antibody-Dependent Cell-Mediated Cytotoxicity (ADCC) against PD-L1 Positive Cells CFSE-labeled Raji-PD-L1 cells (used as target cells) were mixed with NK92MI cells (effector cells) stably expressing FcγRIIIa at a 1:2 ratio, and the mixed cells were cultured for 4 hours at 37° C. under 5%$CO_2$ in the presence of serially diluted IMM2515 or IMM2520. Then propidium iodide (PI) (Cat#P4170, Sigma) was added to the cell culture at a concentration of 5 μg/ml, and the cell culture was subjected to FACS analysis for PI signals. Percentage of cell lysis caused by ADCC was calculated based on the following formula:

%Lysis=(%PI Positive Cell treated with IMM2515 or IMM2520−% PI Positive Cell treated with negative control protein)/(100−% PI Positive Cell treated with negative control protein)*100

Figure 7:
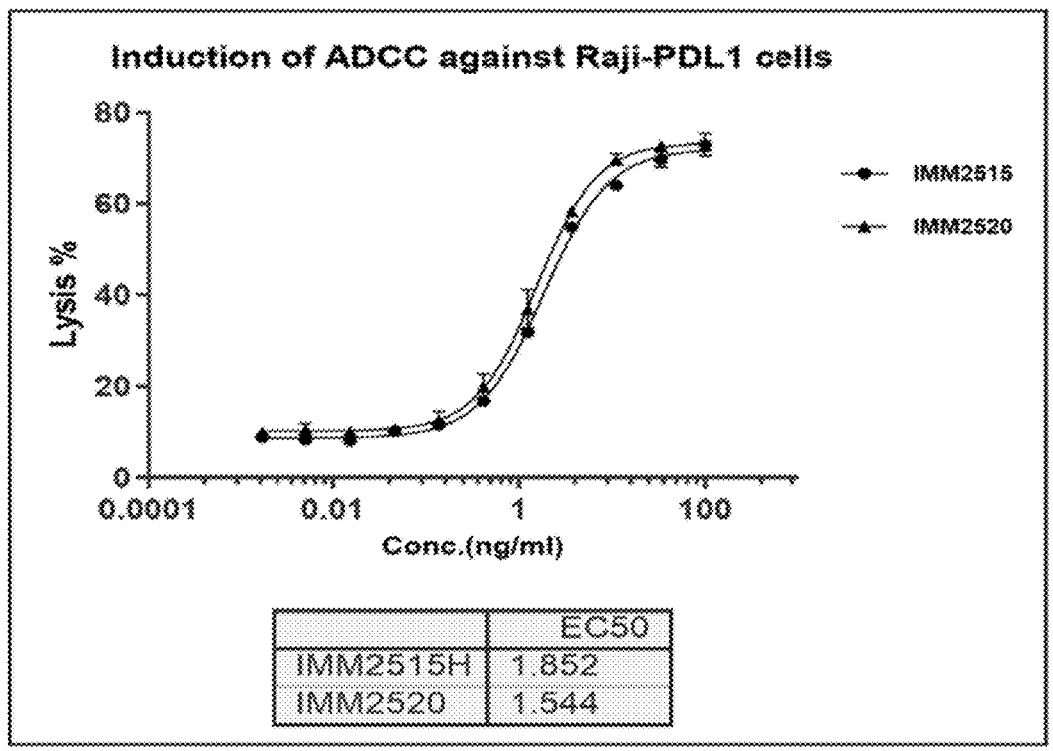
FIG. 7 shows the capability of IMM2520 to induce antibody-dependent cellular cytotoxicity (ADCC) against Raji-PD-L1 cells. IMM2515 is an anti-PD-L1 antibody that constitutes IMM2520 and IMM2521 and comprises the heavy chain of SEQ ID NO: 6 and the light chain of SEQ ID NO: 8.

As shown in FIG. 7, IMM2520 induced higher ADCC level compared to that of the monospecific anti-PD-L1 antibody IMM2515.

Example 7. IMM2520 Induced High Level of Antibody-Dependent Cellular Phagocytosis (Adcp) Against Pd-L1 Positive Cells Ana-1 cells (a mouse macrophage cell line, as effector cells) were seeded in a 96-well cell culture plate, $1 \times 10^5$ cells per well, and cultured for 16-18 hours at 37° C. and 5% $CO_2$. Raji-PD-L1 cells (as target cells) were labeled with CFSE, and then respectively incubated with serially diluted IMM2520, IMM2515, IMM01, the combination of IMM01 and IMM2515,and hIgG1-Fc for 45 minutes. The target cell solutions were transferred to the plate containing Ana-1 cells, the ratio of Ana-1 cells to Raji-PD-L1 cells being 1:1. The mixtures were cultured for 2 hours at the cell culture incubator and then subject to analysis by FACS for the density of CFSE in Ana-1 cells.

Figure 8:
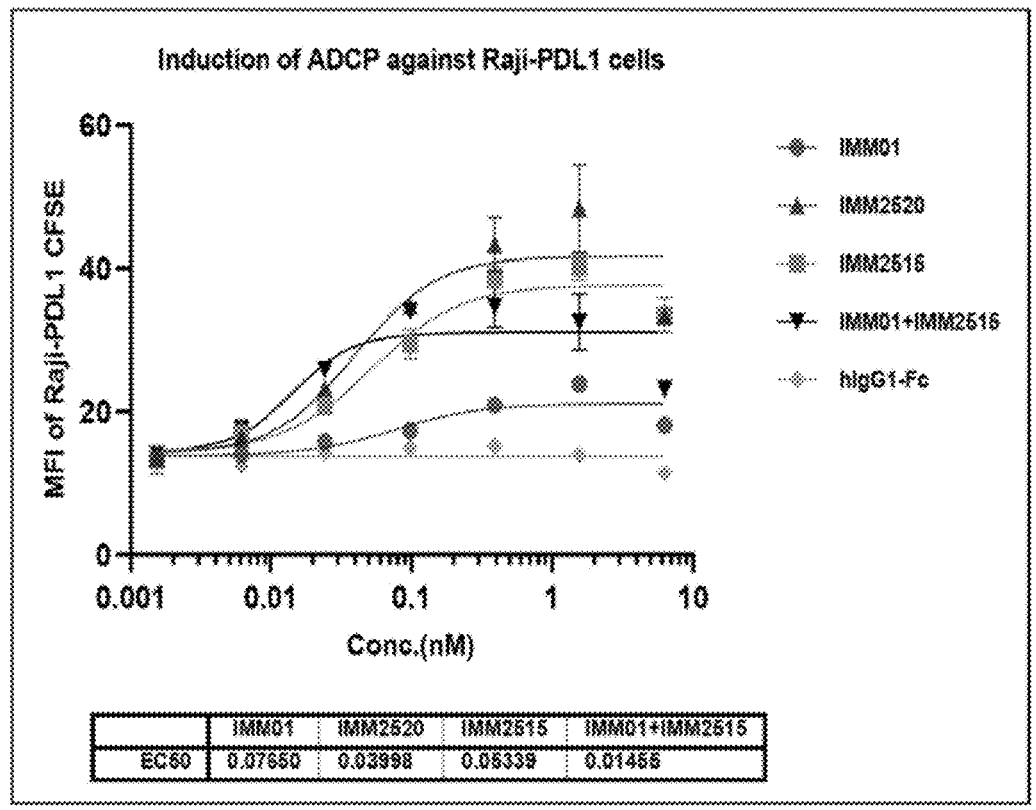
FIG. 8 shows the capability of IMM2520 to induce antibody-dependent cellular phagocytosis (ADCP) against Raji-PD-L1 cells. IMM2515 is an anti-PD-L1 antibody that constitutes IMM2520 and IMM2521 and comprises the heavy chain of SEQ ID NO: 6 and the light chain of SEQ ID NO: 8. IMM01 was described in US 2021/0024598 A1 and comprises two mutated SIRPαD1s (SEQ ID NO: 2) linked to an Fc dimer fragment, whose monomer has the nucleic acid and amino acid sequences of SEQ ID NO: 11 and SEQ ID NO: 12, respectively. The hIgG1-Fc was used as the negative control.

FIG. 8 showed that IMM2520 induced a high level of antibody-dependent cellular phagocytosis (ADCP) against PD-L1+ tumor cells.

Example 8. IMM2520 showed Potent Anti-Tumor Activity

Twenty four 5-7 week old SCID mice were injected subcutaneously with CT26-hPDL1/hCD47 colorectal carcinoma cells, $2\times10^6$ cells per mouse, at the right flank. When tumor volumes reached 100-150 $mm^3$, mice were randomly allocated into four groups with 6 mice in each group, and this day was designated as Day 0. Starting from Day 0, these mice were respectively given intraperitoneal injection of PBS, IMM2505 (6.0 mg/kg), IMM2520 (6.0 mg/kg), and IMM01 (3.0 mg/kg) for 4 weeks, twice per week. Administrations were stopped at the end of week 4 and mice were observed till termination of experiment. For the group with PBS treatment, the test was terminated when the average tumor volume reached 3000 $mm^3$; while for the other groups, the test was terminated at Day 60. Tumor volume and body weight were measured every 3-4 days.

The tumor volume (V) was calculated as (length × $width^2$)/2. Tumor growth inhibition rate (TGI) was calculated by the formula: Tumor growth inhibition rate = (1-tumor volume change in administration group/tumor volume change in control group) ×100%.

The test regime and results were summarized in Table 1.
As shown in Table 1 above and FIGS. 9 and 10, Group 4 had a tumor growth inhibition rate of 97.89%, which was much higher than those of other groups, including the group with IMM2505 treatment. IMM2505 is fusion protein that shares similar overall design with IMM2520 and comprises the mutated SIRPαD1 (SEQ ID NO: 2) and a different anti-PD-L1 antibody. In U.S. Pat. No. 10,973,878 B2, IMM2505 showed superior anti-tumor efficacy over combination of monospecific agents (i.e., anti-PD-L1 antibody combined with IMM01) in a mouse model.

Table 1. Anti-tumor effect of IMM2520 and other agents

TABLE 1

Anti-tumor effect of IMM2520 and other agents

| Group | Drug | Animal # | Dose (mg/kg) | Treatment | TGI | P value |
|---|---|---|---|---|---|---|
| 1 | PBS | 6 | n/a | i.p.b.w. × 4 | | |
| 2 | IMM01 | 6 | 3.0 | i.p.b.w. × 4 | 75.13% | 0.007 |
| 3 | IMM2505 | 6 | 6.0 | i.p.b.w. × 4 | 81.74% | 0.007 |
| 4 | IMM2520 | 6 | 6.0 | i.p.b.w. × 4 | 97.89% | 0.001 |

Figure 9:
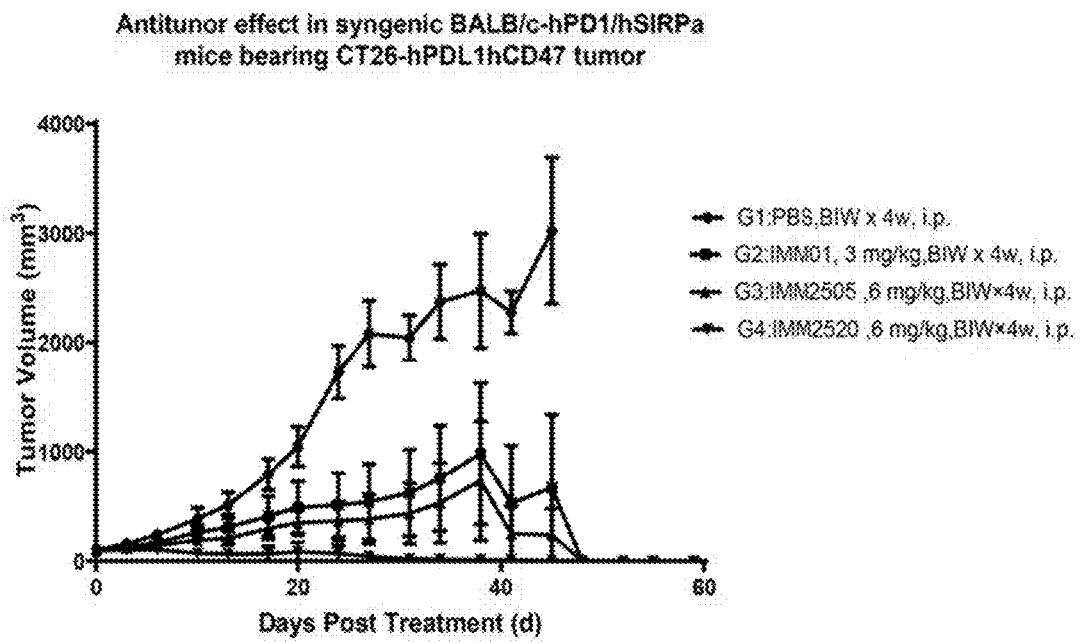
FIG. 9 shows in vivo anti-tumor efficacy of IMM2520 in syngeneic BALB/c-hPD1/hSIRPα mice bearing CT26-hPDL1hCD47 tumor. IMM01 was described in US 2021/0024598 A1 and comprises two mutated SIRPαD1s (SEQ ID NO: 2) linked to an Fc dimer fragment, whose monomer has the nucleic acid and amino acid sequences of SEQ ID NO: 11 and SEQ ID NO: 12, respectively. IMM2505 is a fusion protein described in U.S. Pat. No. 10,973,878 B2 that shares similar overall design with IMM2520 and IMM2521 and comprises the mutated SIRPαD1 (SEQ ID NO: 2) and a different anti-PD-L1 antibody.

As shown in FIG. 9, the tumor sizes of mice in Group 1 kept increasing during the test; in Group 2 and Group 3, with the administration of IMM01 (mutated SIRPαD1-Fc) and IMM2505, respectively, the tumor sizes began to decrease at around Day 40; while in Group 4, the tumor volume declined immediately after IMM2520 administration. The data suggested that IMM2520 acted quickly on the tumors and provided superior anti-tumor efficacy as compared to IMM01 and IMM2505.

Figure 10:
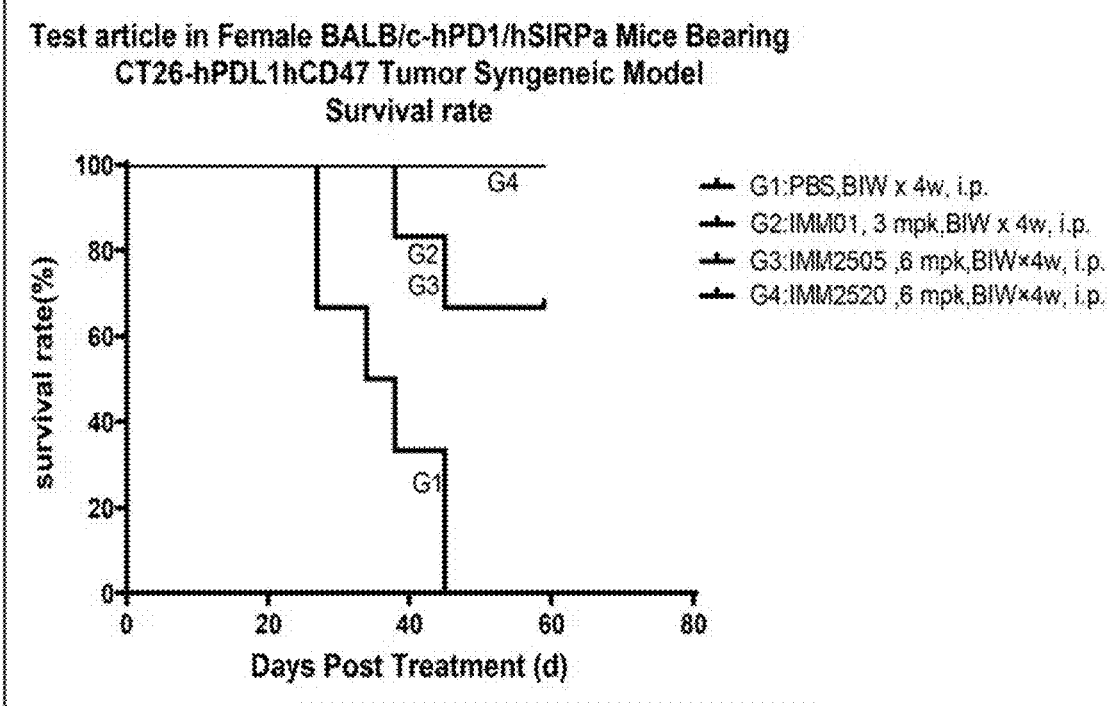
FIG. 10 shows mice treated with IMM2520 had superior survival rate over those treated with IMM2505. IMM2505 is a fusion protein described in U.S. Pat. No. 10,973,878 B2 that shares similar overall design with IMM2520 and IMM2521 and comprises the mutated SIRPαD1 (SEQ ID NO: 2) and a different anti-PD-L1 antibody.

As shown in FIG. 10, Group 2 and Group 3 shared similar survival curves, the survival rates decreased to about 80% around Day 40 and later to about 70%; while the survival rate in Group 4 remained at 100% till Day 60.

Example 9. IMM2520 Simultaneously Bound to PD-L1 and CD47

Molecular interaction device (Probe Life, Gator) was used to detect the simultaneous binding of IMM2520 to CD47 and PD-L1. Anti-human IgG probe was used to capture 10 μg/ml IMM2520 protein until the shift reached ~1.0 nm. The probe was subsequently rinsed in buffer for 30 seconds and then transferred to 10 μg/ml PD-L1-His (FIG. 11) or 10 μg/ml CD47-His solution (FIG. 12) until the binding strength reached saturation levels. Finally, the probe was transferred to 10 μg/ml CD47-His (FIG. 11) or 10 μg/ml PD-L1-His solution (FIG. 12) for 120 seconds.

Figure 11:
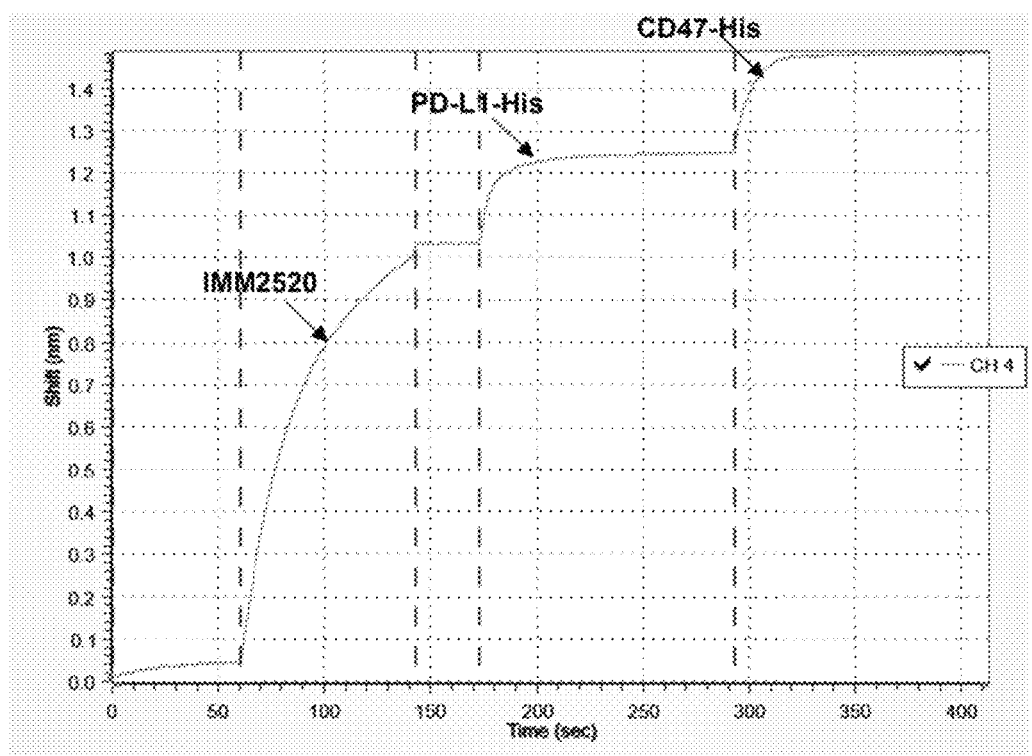
FIG. 11 shows the binding capability of IMM2520, when saturated with PD-L1 binding, to CD47.
Figure 12:
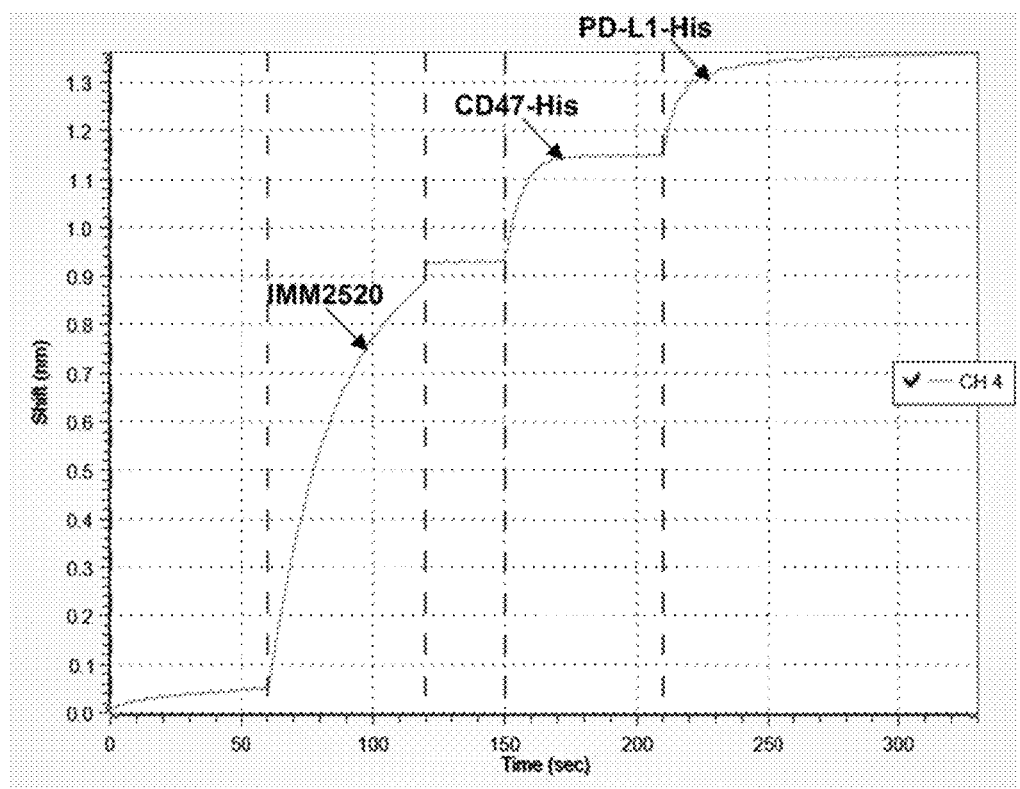
FIG. 12 shows the binding capability of IMM2520, when saturated with CD47 binding, to PD-L1.

As shown in FIG. 11, IMM2520 was able to bind CD47 even when it was saturated with PD-L1 binding; while as shown in FIG. 12, IMM2520 was able to bind PD-L1 after it was saturated with CD47 binding.

Altogether, the data showed that IMM2520, after saturation binding with one antigen, was able to bind to the other antigen, suggesting that it was capable of simultaneously binding to PD-L1 and CD47.

```
                         Description
                     Sequence/SEQ ID NO.
```

Nucleic acid sequence of first extracellular Ig-like domain of SIRP alpha (SIRPαD1) with mutation
GAGGAGGAGCTGCAGGTGATTCAGCCTGACAAGTCCGTATCAGTTGCAGCTGGAGAGTC
GGCCATTCTGCACTGCACTGTGACCTCCCTGATCCCTGTGGGGCCCATCCAGTGGTTCAG
AGGAGCTGGACCAGCCCGGGAATTAATCTACAATCAAAAAGAAGGCCACTTCCCCCGGG
TAACAACTGTTTCAGAGTCCACAAAGAGAGAAAACATGGACTTTTCCATCAGCATCAGT
GCCATCACCCCAGCAGATGCCGGCACCTACTACTGTGTGAAGTTCCGGAAAGGGAGCCC
TGACACGGAGTTTAAGTCTGGAGCAGGCACTGAGCTGTCTGTGCGTGCCAAACCCTCTGC
CCCCGTGGTATCGGGCCCT (SEQ ID NO: 1)

Amino acid sequence of SIRPαD1 mutant
EEELQVIQPDKSVSVAAGESAILHCTVTSLIPVGPIQWFRGAGPARELIYNQKEGHFPRVTTVS
ESTKRENMDFSISISAITPADAGTYYCVKFRKGSPDTEFKSGAGTELSVRAKPSAPVVSGP
(SEQ ID NO: 2)

| Description | Sequence/SEQ ID NO. |
|---|---|

Nucleic acid sequence of linker
GGCGGCGGTGGGAGCGGCGGCGGTGGGAGCGGCGGCGGGGGCTCG (SEQ ID NO: 3)

Amino acid sequence of linker
GGGGSGGGGSGGGGS (SEQ ID NO: 4)

Nucleic acid sequence of heavy chain of anti-PD-L1 antibody
CAAGTGCAGCTGGTGCAGAGCGGCGCCGAGGTGAAGAAGCCTGGCGCAAGCGTGAAGG
TGAGCTGCAAGGCAAGCGGCTACACCTTCACAAGCAACTGGATGCACTGGGTGAGACAA
GCCCCTGGCCAAGGCCTGGAGTGGATGGGCATGATCCACCCTAACAGCGGCAGCAGCAA
CTACAACGAGAAGTTCAAGAGCAGAGTGACCATGACAAGAGACACAAGCACAAGCACC
GTGTACATGGAGCTGAGCAGCCTGAGAAGCGAGGACACCGCCGTGTACTACTGCGCTAG
AAGCTACTACGGCAGCAGCCCTTACTACTTCGACTACTGGGGCCAAGGCACCCTGGTGAC
CGTGAGCAGCGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGGCTGTCCT
ACAGTCCTCAGGACTCTACTCCCTCAGCAGCGTGGTGACCGTGCCCTCCAGCAGCTTGGG
CACCCAGACCTACATCTGCAACGTGAATCACAAGCCCAGCAACACCAAGGTGGACAAGA
GAGTTGAGCCCAAATCTTGTGACAAAACTCACACATGCCCACCGTGCCCAGCACCTGAA
CTCCTGGGGGGACCGTCAGTCTTCCTCTTCCCCCCAAAACCCAAGGACACCCTCATGATC
TCCCGGACCCCTGAGGTCACATGCGTGGTGGTGGACGTGAGCCACGAAGACCCTGAGGT
CAAGTTCAACTGGTATGTGGACGGCGTGGAGGTGCATAATGCCAAGACAAAGCCGCGGG
AGGAGCAGTACAACGCCACGTACCGTGTGGTCAGCGTCCTCACCGTCCTGCACCAAGAC
TGGCTGAATGGCAAGGAGTACAAGTGCAAGGTCTCCAACAAAGCCCTCCCAGCCCCCAT
CGCCGCAACCATCTCCAAAGCCAAAGGGCAGCCCCGAGAACCACAGGTGTACACCCTGC
CCCCATCCCGGGAGGAGATGACCAAGAACCAAGTCAGCCTGACCTGCCTGGTCAAAGGC
TTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTATTCCAAGCTCACC
GTGGACAAGAGCAGGTGGCAGCAGGGGAACGTCTTCTCATGCTCCGTGATGCATGAGGC
TCTGCACAACCACTACACGCAGAAGAGCCTCTCCCTGTCTCCGGGCAAATGA (SEQ ID NO: 5)

Amino acid sequence of heavy chain of anti-PD-L1 antibody
QVQLVQSGAEVKKPGASVKVSCKASGYTFTSNWMHWVRQAPGQGLEWMGMIHPNSGSSN
YNEKFKSRVTMTRDTSTSTVYMELSSLRSEDTAVYYCARSYYGSSPYYFDYWGQGTLVTVS
SASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPREEQYNATYRVVS
VLTVLHQDWLNGKEYKCKVSNKALPAPIAATISKAKGQPREPQVYTLPPSREEMTKNQVSLT
CLVKGFYPSDIAVEWESNGQPENNYKTTPPVLDSDGSFFLYSKLTVDKSRWQQGNVFSCSV
MHEALHNHYTQKSLSLSPGK (SEQ ID NO: 6)

Nucleic acid sequence of light chain of anti-PD-L1 antibody
GACATTCAGATGACACAGAGCCCTAGCAGCCTGAGCGCAAGCGTGGGCGACAGAGTGAC
CATCACCTGCAGAGCAAGCCAAGACATCATCAACTACCTGAACTGGTATCAGCAGAAGC
CTGGCAAGGCCCCTAAGCTGCTGATCTACTACACAAGCAGACTGCACAGCGGCGTGCCT
AGCAGATTCAGCGGCAGCGGCAGCGGCACCGACTTCACCTTCACCATCAGCAGCCTGCA
GCCTGAGGACATCGCCACCTACTACTGTCAGCAAGGCGACACCCTGCCTTGGACCTTCGG
CCAAGGCACCAAGGTGGAGATCAAGCGAACTGTGGCTGCACCATCTGTCTTCATCTTCCC
GCCATCTGATGAGCAGTTGAAATCTGGAACTGCCTCTGTTGTGTGCCTGCTGAATAACTT
CTATCCCAGAGAGGCCAAAGTACAGTGGAAGGTGGATAACGCCCTCCAATCGGGTAACT
CCCAGGAGAGTGTCACAGAGCAGGACAGCAAGGACAGCACCTACAGCCTCAGCAGCAC
CCTGACGCTGAGCAAAGCAGACTACGAGAAACACAAAGTCTACGCCTGCGAAGTCACCC
ATCAGGGCCTGAGCTCGCCCGTCACAAAGAGCTTCAACAGGGGAGAGTGTTAG (SEQ ID NO: 7)

Amino acid sequence of light chain of anti-PD-L1 antibody
DIQMTQSPSSLSASVGDRVTITCRASQDIINYLNWYQQKPGKAPKLLIYYTSRLHSGVPSRFSG
SGSGTDFTFTISSLQPEDIATYYCQQGDTLPWTFGQGTKVEIKRTVAAPSVIFPPSDEQLKSGT
ASVVCLLNNFYPREAKVQWKVDNALQSGNSQESVTEQDSKDSTYSLSSTLTLSKADYEKHK
VYACEVTHQGLSSPVTKSFNRGEC (SEQ ID NO: 8)

Nucleic acid sequence of SIRPαD1 mutant-linker-anti-PD-L1 heavy chain variable region-heavy chain constant region
GAGGAGGAGCTGCAGGTGATTCAGCCTGACAAGTCCGTATCAGTTGCAGCTGGAGAGTC
GGCCATTCTGCACTGCACTGTGACCTCCCTGATCCCTGTGGGGCCCATCCAGTGGTTCAG
AGGAGCTGGACCAGCCCGGGAATTAATCTACAATCAAAAGAAGGCCACTTCCCCCGGG
TAACAACTGTTTCAGAGTCCACAAAGAGAGAAAACATGGACTTTTCCATCAGCATCAGT
GCCATCACCCCAGCAGATGCCGGCACCTACTACTGTGTGAAGTTCCGGAAAGGGAGCCC
TGACACGGAGTTTAAGTCTGGAGCAGGCACTGAGCTGTCTGTGCGTGCCAAACCCTCTGC
CCCCGTGGTATCGGGCCCTGGCGGCGGTGGGAGCGGCGGCGGTGGGAGCGGCGGCGGG
GGCTCGCAAGTGCAGCTGGTGCAGAGCGGCGCCGAGGTGAAGAAGCCTGGCGCAAGCGT
GAAGGTGAGCTGCAAGGCAAGCGGCTACACCTTCACAAGCAACTGGATGCACTGGGTGA
GACAAGCCCCTGGCCAAGGCCTGGAGTGGATGGGCATGATCCACCCTAACAGCGGCAGC
AGCAACTACAACGAGAAGTTCAAGAGCAGAGTGACCATGACAAGAGACACAAGCACAA

| Description<br>Sequence/SEQ ID NO. |
|---|
| GCACCGTGTACATGGAGCTGAGCAGCCTGAGAAGCGAGGACACCGCCGTGTACTACTGC<br>GCTAGAAGCTACTACGGCAGCAGCCCTTACTACTTCGACTACTGGGGCCAAGGCACCCTG<br>GTGACCGTGAGCAGCGCTAGCACCAAGGGCCCATCGGTCTTCCCCCTGGCACCCTCCTCC<br>AAGAGCACCTCTGGGGGCACAGCGGCCCTGGGCTGCCTGGTCAAGGACTACTTCCCCGA<br>ACCGGTGACGGTGTCGTGGAACTCAGGCGCCCTGACCAGCGGCGTGCACACCTTCCCGG<br>CTGTCCTACAGTCCTCAGGACTCTACTCCCTCAGCAGCGTGGTGACCGTGCCCTCCAGCA<br>GCTTGGGCACCCAGACCTACATCTGCAACGTGAATCACAAGCCCAGCAACACCAAGGTG<br>GACAAGAGAGTTGAGCCCAAATCTTGTGACAAAACTCACACATGCCCACCGTGCCCAGC<br>ACCTGAACTCCTGGGGGACCGTCAGTCTTCCTCTTCCCCCCAAAACCCAAGGACACCCT<br>CATGATCTCCCGGACCCCTGAGGTCACATGCGTGGTGGTGGACGTGAGCCACGAAGACC<br>CTGAGGTCAAGTTCAACTGGTATGTGGACGGCGTGGAGGTGCATAATGCCAAGACAAAG<br>CCGCGGGAGGAGCAGTACAACGCCACGTACCGTGTGGTCAGCGTCCTCACCGTCCTGCA<br>CCAAGACTGGCTGAATGGCAAGGAGTACAAGTGCAAGGTCTCCAACAAAGCCCTCCCAG<br>CCCCCATCGCCGCAACCATCTCCAAAGCCAAAGGGCAGCCCCGAGAACCACAGGTGTAC<br>ACCCTGCCCCCATCCCGGGAGGAGATGACCAAGAACCAAGTCAGCCTGACCTGCCTGGT<br>CAAAGGCTTCTATCCCAGCGACATCGCCGTGGAGTGGGAGAGCAATGGGCAGCCGGAGA<br>ACAACTACAAGACCACGCCTCCCGTGCTGGACTCCGACGGCTCCTTCTTCCTCTATTCCA<br>AGCTCACCGTGGACAAGAGCAGGTGGCAGCAGGGGAACGTCTTCTCATGCTCCGTGATG<br>CATGAGGCTCTGCACAACCACTACACGCAGAAGAGCCTCTCCCTGTCTCCGGGCAAATG<br>A (SEQ ID NO: 9) |
| Amino acid sequence of SIRPαD1 mutant-linker-anti-PD-L1 heavy chain variable region-heavy chain<br>constant region<br>EEELQVIQPDKSVSVAAGESAILHCTVTSLIPVGPIQWFRGAGPARELIYNQKEGHFPRVTTVS<br>ESTKRENMDFSISISAITPADAGTYYCVKFRKGSPDTEFKSGAGTELSVRAKPSAPVVSGPGG<br>GGSGGGGSGGGGSQVQLVQSGAEVKKPGASVKVSCKASGYTFTSNWMHWVRQAPGQGLE<br>WMGMIHPNSGSSNYNEKFKSRVTMTRDTSTSTVYMELSSLRSEDTAVYYCARSYYGSSPYY<br>FDYWGQGTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSCDKTHTCPP<br>CPAPELLGGPSVFLFPPKPKDTLMISRTPEVTCVVVDVSHEDPEVKFNWYVDGVEVHNAKTK<br>PREEQYNATYRVVSVLTVLHQDWLNGKEYKCKVSNKALPAPIAATISKAKGQPREPQVYTL<br>PPSREEMTKNQVSLTCLVKGFYPSDIAVEWESNGQPENNYKTTPPVLDSDGSFFLYSKLTVD<br>KSRWQQGNVFSCSVMHEALHNHYTQKSLSLSPGK (SEQ ID NO: 10) |
| Nucleic acid sequence of SIRPαD1 mutant-Fc<br>GAGGAGGAGCTGCAGGTGATTCAGCCTGACAAGTCCGTATCAGTTGCAGCTGGAGAGTC<br>GGCCATTCTGCACTGCACTGTGACCTCCCTGATCCCTGTGGGGCCCATCCAGTGGTTCAG<br>AGGAGCTGGACCAGCCCGGGAATTAATCTACAATCAAAAGAAGGCCACTTCCCCCGGG<br>TAACAACTGTTTCAGAGTCCACAAAGAGAGAAAACATGGACTTTTCCATCAGCATCAGT<br>GCCATCACCCCAGCAGATGCCGGCACCTACTACTGTGTGAAGTTCCGGAAAGGGAGCCC<br>TGACACGGAGTTTAAGTCTGGAGCAGGCACTGAGCTGTCTGTGCGTGCCAAACCCTCTGC<br>CCCCGTGGTATCGGGCCCTGCGGCGAGGGCCACACCTCAGCACGAGCCCAAATCTTGTG<br>ACAAAACTCACACATGCCCACCGTGCCCAGCACCTGAACTCCTGGGGGACCGTCAGTC<br>TTCCTCTTCCCCCCAAAACCCAAGGACACCCTCATGATCTCCCGGACCCCTGAGGTCACA<br>TGCGTGGTGGTGGACGTGAGCCACGAAGACCCTGAGGTCAAGTTCAACTGGTACGTGGA<br>CGGCGTGGAGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGGCAAGGAGTAC<br>AAGTGCAAGGTCTCCAACAAAGCCCTCCCAGCCCCCATCGAGAAAACATCTCCAAAGC<br>CAAAGGGCAGCCCCGAGAACCACAGGTGTACACCCTGCCCCCATCCCGGGATGAGCTGA<br>CCAAGAACCAGGTCAGCCTGACCTGCCTGGTCAAAGGCTTCTATCCCAGCGACATCGCCG<br>TGGAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCACTACACGCAG<br>AAGAGCCTCTCCCTGTCTCCGGGTTGA (SEQ ID NO: 11) |
| Amino acid sequence of SIRPαD1 mutant-Fc<br>EEELQVIQPDKSVSVAAGESAILHCTVTSLIPVGPIQWFRGAGPARELIYNQKEGHFPRVTTVS<br>ESTKRENMDFSISISAITPADAGTYYCVKFRKGSPDTEFKSGAGTELSVRAKPSAPVVSGPAAR<br>ATPQHEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSPG (SEQ ID NO: 12) |
| Nucleic acid sequence of signal peptide of mouse IgG1 heavy chain<br>ATGGGATGGTCATGTATCATCCTTTTTCTGGTAGCAACTGCAACTGGAGTACATTCA (SEQ<br>ID NO: 13) |
| Kozak<br>GCCGCCACC (SEQ ID NO: 14) |
| Nucleic acid sequence of SIRPαD1 mutant-linker-anti-PD-L1 light chain variable region-light chain<br>constant region<br>GAGGAGGAGCTGCAGGTGATTCAGCCTGACAAGTCCGTATCAGTTGCAGCTGGAGAGTC<br>GGCCATTCTGCACTGCACTGTGACCTCCCTGATCCCTGTGGGGCCCATCCAGTGGTTCAG<br>AGGAGCTGGACCAGCCCGGGAATTAATCTACAATCAAAAGAAGGCCACTTCCCCCGGG<br>TAACAACTGTTTCAGAGTCCACAAAGAGAGAAAACATGGACTTTTCCATCAGCATCAGT |

| Description Sequence/SEQ ID NO. |
|---|
| GCCATCACCCCAGCAGATGCCGGCACCTACTACTGTGTGAAGTTCCGGAAAGGGAGCCC<br>TGACACGGAGTTTAAGTCTGGAGCAGGCACTGAGCTGTCTGTGCGTGCCAAACCCTCTGC<br>CCCCGTGGTATCGGGCCCTGGCGGCGGTGGGAGCGGCGGCGGTGGGAGCGGCGGCGGG<br>GGCTCGGACATTCAGATGACACAGAGCCCTAGCAGCCTGAGCGCAAGCGTGGGCGACAG<br>AGTGACCATCACCTGCAGAGCAAGCCAAGACATCATCAACTACCTGAACTGGTATCAGC<br>AGAAGCCTGGCAAGGCCCCTAAGCTGCTGATCTACTACACAAGCAGACTGCACAGCGGC<br>GTGCCTAGCAGATTCAGCGGCAGCGGCAGCGGCACCGACTTCACCTTCACCATCAGCAG<br>CCTGCAGCCTGAGGACATCGCCACCTACTACTGTCAGCAAGGCGACACCCTGCCTTGGAC<br>CTTCGGCCAAGGCACCAAGGTGGAGATCAAGCGTGAGTTCTAGAGGATCCATCTGGGAT<br>AAGCATGCTGTTTTCTGTCTGTCCCTAACATGCCCTGTGATTATCGCAAACAACACACC<br>CAAGGGCAGAACTTTGTTACTTAAACACCATCCTGTTTGCTTCTTTCCTCAGGAACTGTGG<br>CTGCACCATCTGTCTTCATCTTCCCGCCATCTGATGAGCAGTTGAAATCTGGAACTGCCTC<br>TGTTGTGTGCCTGCTGAATAACTTCTATCCCAGAGAGGCCAAAGTACAGTGGAAGGTGG<br>ATAACGCCCTCCAATCGGGTAACTCCCAGGAGAGTGTCACAGAGCAGGACAGCAAGGAC<br>AGCACCTACAGCCTCAGCAGCACCCTGACGCTGAGCAAAGCAGACTACGAGAAACACAA<br>AGTCTACGCCTGCGAAGTCACCCATCAGGGCCTGAGCTCGCCCGTCACAAAGAGCTTCA<br>ACAGGGGAGAGTGTTAG (SEQ ID NO: 15) |

Amino acid sequence of SIRPαD1 mutant-linker-anti-PD-L1 light chain variable region-light chain constant region
EEELQVIQPDKSVSVAAGESAILHCTVTSLIPVGPIQWFRGAGPARELIYNQKEGHFPRVTTVS
ESTKRENMDFSISISAITPADAGTYYCVKFRKGSPDTEFKSGAGTELSVRAKPSAPVVSGPGG
GGGSGGGGSGGGGSDIQMTQSPSSLSASVGDRVTITCRASQDIINYLNWYQQKPGKAPKLLIYY
TSRLHSGVPSRFSGSGSGTDFTFTISSLQPEDIATYYCQQGDTLPWTFGQGTKVEIKRTVAAPS
VFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 16)

Amino acid sequence of linker
GGGGSGGGGS (SEQ ID NO: 17)

Amino acid sequence of linker
GGGGSGGGGSGGGGSGGGGS (SEQ ID NO: 18)

Amino acid sequence of anti-PD-L1 heavy chain variable region
QVQLVQSGAEVKKPGASVKVSCKASGYTFTSNWMHWVRQAPGQGLEWMGMIHPNSGSSN
YNEKFKSRVTMTRDTSTSTVYMELSSLRSEDTAVYYCARSYYGSSPYYFDYWGQGTLVTVS
S (SEQ ID NO: 19)

Amino acid sequence of anti-PD-L1 light chain variable region
DIQMTQSPSSLSASVGDRVTITCRASQDIINYLNWYQQKPGKAPKLLIYYTSRLHSGVPSRFSG
SGSGTDFTFTISSLQPEDIATYYCQQGDTLPWTFGQGTKVEIK (SEQ ID NO: 20)

Amino acid sequence of heavy chain constant region
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNATYRVVSV
LTVLHQDWLNGKEYKCKVSNKALPAPIAATISKAKGQPREPQVYTLPPSREEMTKNQVSLTC
LVKGFYPSDIAVEWESNGQPENNYKTTPPVLDSDGSFFLYSKLTVDKSRWQQGNVFSCSVM
HEALHNHYTQKSLSLSPGK (SEQ ID NO: 21)

Amino acid sequence of human PD-1 with mouse IgG1 Fc
MGWSCIILFLVATATGVHSLDSPDRPWNPPTFSPALLVVTEGDAATFTCSFSNTSESFVLNWY
RMSPSNQTDKLAAFPEDRSQPGQDCRFRVTQLPNGRDFHMSVVRARRNDSGTYLCGAISLAP
KAQIKESLRAELRVTERRAEVPTAHPSPSPRPAGQFQEFVPRDCGCKPCICTVPEVSSVFIFPPK
PKDVLTITLTPKVTCVVVDISKDDPEVQFSWFVDDVEVHTAQTQPREEQFNSTFRSVSELPIM
HQDWLNGKEFKCRVNSAAFPAPIEKTISKTKGRPKAPQVYTIPPPKEQMAKDKVSLTCMITDF
FPEDITVEWQWNGQPAENYKNTQPIMNTNGSYFVYSKLNVQKSNWEAGNTFTCSVLHEGLH
NHHTEKSLSHSPGK (SEQ ID NO: 22)

Amino acid sequence of wild type human SIRPa with human IgG1 Fc
MGWSCIILFLVATATGVHSSCAWSGVAGEEELQVIQPDKSVSVAAGESAILHCTVTSLIPVGPI
QWFRGAGPARELIYNQKEGHFPRVTTVSESTKRENMDFSISISNITPADAGTYYCVKFRKGSP
DTEFKSGAGTELSVRAKPSAPVVSGPAARATPQHTVSFTCESHGFSPRDITLKWFKNGNELSD
FQTNVDPVGESVSYSIHSTAKVVLTREDVHSQVICEVAHVTLQGDPLRGTANLSETIRVPPTL
EVTQQPVRAENQVNVTCQVRKFYPQRLQLTWLENGNVSRTETASTVTENKDGTYNWMSWL
LVNVSAHRDDVKLTCQVEHDGQPAVSKSHDLKVSAHPKEQGSNTAAENTGSNERNEFEPKS
CDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGK (SEQ ID NO: 23)

While the application has been described above in connection with one or more embodiments, it should be understood that the application is not limited to those embodiments, and the description is intended to cover all alternatives, modifications, and equivalents, as may be included within the spirit and scope of the appended claims. All references cited herein are further incorporated by reference in their entirety.

REFERENCES

1. Fife B T, Pauken K E. The role of the PD-1 pathway in autoimmunity and peripheral tolerance. Annals of the New York Academy of Sciences. 2011, 1217: 45-59
2. Francisco L M, Sage P T, Sharpe A H. The PD-1 pathway in tolerance and autoimmunity. Immunological Reviews. 2010, 236: 219-42
3. Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334
4. Gennaro, ed., Remington: The Science and Practice of Pharmacy, 20th Ed., Lippincott Williams & Wilkins 2003
5. J. R. Robinson, ed., Sustained and Controlled Release Drug Delivery Systems, Marcel Dekker, Inc., New York, 1978
6. Lee W Y, Weber D A, Laur O, Severson E A, McCall I, Jen R P, Chin A C, Wu T, Gernert KM, Parkos C A. Novel Structural Determinants on SIRPa that Mediate Binding to CD47. J Immunol. 2007, 179:7741-7750
7. Obeid M, Panaretakis T, Joza N, Tufi R, Tesniere A, van Endert P, Zitvogel L, Kroemer G. Calreticulin exposure is required for the immunogenicity of gamma-irradiation and UVC lightinduced apoptosis. Cell Death Differ. 2007, 14:1848-1850
8. Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003, 161:1179-1189
9. Shields R L, Namenuk A K, Hong K, Meng Y G, Rae J, Briggs J, Xie D, Lai J, Stadlen A, Li B, Fox J A, Presta L G. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604
10. Suzanne L. Topalian, F. Stephen Hodi, Julie R. Brahmer, Scott N. Gettinger, David C. Smith, David F. McDermott, John D. Powderly, Richard D. Carvajal, Jeffrey A. Sosman, Michael B. Atkins, Philip D. Leming, David R. Spigel, Scott J. Antonia, Leora Horn, Charles G. Drake, Drew M. Pardoll, Lieping Chen, William H. Sharfman, Robert A. Anders, Janis M. Taube, Tracee L. McMiller, Haiying Xu, Alan J. Korman, Maria Jure-Kunkel, Shruti Agrawal, Daniel McDonald, Georgia D. Kollia, Ashok Gupta, Jon M. Wigginton, and Mario Sznol. Safety, Activity, and Immune Correlates of Anti-PD-1 Antibody in Cancer, N Engl J Med 2012; 366:2443-2454
11. Theocharides, A. P. A. ; Jin, L. Q. ; Cheng, P. Y. ; Prasolava, T. K. ; Malko, A. V. ; Ho, J. M.; Poeppl, A. G. ; Rooijen, N. van ; Minden, M. D. ; Danska, J. S. ; Dick, J. ; Wang, J. C. Y. J. Exp. Med. 2012, Vol. 209 No. 10 1883-1899
12. Thompson R H, Gillett M D, Cheville J C, Lohse C M, Dong H, Webster W S, Krejci K G, Lobo J R, Sengupta S, Chen L, Zincke H, Blute M L, Strome S E, Leibovich B C, Kwon E D. Costimulatory B7-H1 in renal cell carcinoma patients: Indicator of tumor aggressiveness and potential therapeutic target. PNAS. 2004, 101 (49): 17174-9
13. Tseng D, Volkmer J P, Willingham S B, Contreras-Trujillo H, Fathman J W, Fernhoff N B, Seita J, Inlay M A, Weiskopf K, Miyanishi M, Weissman I L. Anti-CD47 antibody-mediated phagocytosis of cancer by macrophages primes an effective antitumor T-cell response. PNAS. 2013, 110:11103-11108
14. Vlahopoulos, S A. Aberrant control of NF-κB in cancer permits transcriptional and phenotypic plasticity, to curtail dependence on host tissue: molecular mode. Cancer biology & medicine. 2017, 14: 254-270
15. Shim H. Bispecific Antibodies and Antibody-Drug Conjugates for Cancer Therapy: Technological Considerations. Biomolecules. 2020 Feb. 26;10(3):360
16. Wang S, Chen K, Lei Q, Ma P, Yuan A Q, Zhao Y, Jiang Y, Fang H, Xing S, Fang Y, Jiang N, Miao H, Zhang M, Sun S, Yu Z, Tao W, Zhu Q, Nie Y, Li N. The state of the art of bispecific antibodies for treating human malignancies. EMBO Mol Med. 2021 Aug. 24:e14291. doi: 10.15252/emmm.202114291

The invention claimed is:

1. A recombinant fusion protein, comprising an anti-PD-L1 antibody or an antigen binding fragment thereof, and a CD47 binding peptide,
   wherein the anti-PD-L1 antibody or antibody fragment thereof is linked to the CD47 binding peptide at the N-terminus of a heavy chain variable region or the a chain variable region,
   wherein each of the anti-PD-L1 antibody or the antigen binding fragment thereof comprises SEQ ID NO: 19 and SEQ ID NO: 20,
   wherein the CD47 binding peptide comprises a signal-regulatory protein (SIRP) extracellular domain comprising SEQ ID NO: 2,
   wherein the recombinant fusion protein is capable of binding to CD47 and PD-L1 simultaneously.

2. The recombinant fusion protein of claim 1, wherein the anti-PD-L1 antibody or antibody fragment thereof is linked to the CD47 binding peptide at the N-terminus of the heavy chain variable region.

3. The recombinant fusion protein of claim 1, wherein the anti-PD-L1 antibody or antibody fragment thereof is linked to the CD47 binding peptide at N-terminus of the light chain variable region.

4. The recombinant fusion protein of claim 1, wherein the anti-PD-L1 antibody or antibody fragment thereof is linked to the CD47 binding peptide via a linker.

5. The recombinant fusion protein of claim 4, wherein the linker is SEQ ID NO: 4.

6. The recombinant fusion protein of claim 2, comprising SEQ ID NO: 10.

7. The recombinant fusion protein of claim 2, further comprising SEQ ID NO: 8.

8. The recombinant fusion protein of claim 3, further comprising a light chain constant region linked to the light chain variable region, wherein the recombinant fusion protein comprises an anti-PD-L1 heavy chain variable region-heavy chain constant region fragment comprising SEQ ID NO: 6, and a CD47binding peptide-linker-anti-PD-L1 light chain variable region-light chain constant region fragment having an amino acid sequence comprising SEQ ID NO: 16.

9. The recombinant fusion protein of claim 1, comprising a heavy chain constant region comprising SEQ ID NO: 21.

10. An isolated nucleic acid molecule encoding the recombinant fusion protein of claim 1.

11. An isolated expression vector comprising the nucleic acid molecule of claim 10.

12. An isolated host cell comprising the expression vector of claim 11.

13. A pharmaceutical composition, comprising the recombinant fusion protein of claim 11, and at least one pharmaceutically acceptable excipient.

14. The pharmaceutical composition of claim 13, further comprising at least one pharmaceutically acceptable adjuvant.

15. A method for treating a disease associated with target cells that are double positive for CD47 and PD-L1 in a subject in need thereof, wherein the disease is non-Hodgkin's lymphoma (NHL) or colon cancer, comprising administering to the subject the pharmaceutical composition of claim 13.

* * * * *

SEQUENCE LISTING

```
<160> NUMBER OF SEQ ID NOS: 23

<210> SEQ ID NO 1
<211> LENGTH: 375
<212> TYPE: DNA
<213> ORGANISM: Artificial Sequence
<220> FEATURE:
<223> OTHER INFORMATION: SIRPaD1 mutant

<400> SEQUENCE: 1
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt cccccgggta     180
acaactgttt cagagtccac aaagagagaa aacatggact tttccatcag catcagtgcc     240 atcacccag cagatgccgg cacctactac tgtgtgaagt tccggaaagg gagccctgac      300
acggagttta gtctggagc aggcactgag ctgtctgtgc gtgccaaacc ctctgccccc      360
gtggtatcgg gccct                                                     375
```

```
<210> SEQ ID NO 2
<211> LENGTH: 125
<212> TYPE: PRT
<213> ORGANISM: Artificial Sequence
<220> FEATURE:
<223> OTHER INFORMATION: SIRPaD1 mutant

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro
        115                 120                 125

<210> SEQ ID NO 3
<211> LENGTH: 45
<212> TYPE: DNA
<213> ORGANISM: Artificial Sequence
<220> FEATURE:
<223> OTHER INFORMATION: Linker

<400> SEQUENCE: 3
ggcggcggtg ggagcggcgg cggtgggagc ggcggcgggg gctcg                45

<210> SEQ ID NO 4
<211> LENGTH: 15
<212> TYPE: PRT
<213> ORGANISM: Artificial Sequence
<220> FEATURE:
<223> OTHER INFORMATION: Linker

<400> SEQUENCE: 4

Gly Gly Gly Gly Ser Gly Gly Gly Ser Gly Gly Gly Gly Ser
1               5                   10                  15

<210> SEQ ID NO 5
<211> LENGTH: 1356
<212> TYPE: DNA
<213> ORGANISM: Artificial Sequence
<220> FEATURE:
<223> OTHER INFORMATION: Heavy chain of anti-PD-L1 antibody IMM2515

<400> SEQUENCE: 5
caagtgcagc tggtgcagag cggcgccgag gtgaagaagc ctggcgcaag cgtgaaggtg    60
agctgcaagg caagcggcta caccttcaca agcaactgga tgcactgggt gagacaagcc   120
cctggccaag gcctggagtg gatgggcatg atccacccta acagcggcag cagcaactac   180
aacgagaagt tcaagagcag agtgaccatg acaagagaca agagcacaag caccgtgtac   240
atggagctga gcagcctgag aagcgaggac accgccgtgt actactgcgc tagaagctac   300
tacggcagca gccccttacta cttcgactac tggggccaag gcaccctggt gaccgtgagc   360
```

```
agcgctagca ccaagggccc atcggtcttc ccctggcac cctcctccaa gagcacctct    420
gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtatgtgg acggcgtgga ggtgcataat gccaagacaa agccgcggga ggagcagtac    900
aacgccacgt accgtgtggt cagcgtcctc accgtcctgc accagactg gctgaatggc    960 aaggagtaca gtgcaaggt ctccaacaaa gccctcccag ccccatcgc cgcaaccatc   1020 tccaaagcca agggcagcc ccgagaacca caggtgtaca ccctgccccc atcccgggag   1080
gagatgacca gaaccaagt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tattccaagc tcaccgtgga caagagcagg   1260
tggcagcagg ggaacgtctt ctcatgctcc gtgatgcatg aggctctgca caaccactac   1320
acgcagaaga gcctctccct gtctccgggc aaatga                           1356
```

<210> SEQ ID NO 6
<211> LENGTH: 451
<212> TYPE: PRT
<213> ORGANISM: Artificial Sequence
<220> FEATURE:
<223> OTHER INFORMATION: Heavy chain of anti-PD-L1 antibody IMM2515

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Arg Gln Ala Pro Gly Gln Gly Leu Glu Trp Met
        35                  40                  45

Gly Met Ile His Pro Asn Ser Gly Ser Ser Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Gly Ser Ser Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

|   |   |   | 180 |   |   | 185 |   |   | 190 |   |   |
|---|---|---|---|---|---|---|---|---|---|---|---|

Pro Ser Ser Ser Leu Gly Thr Gln Thr Tyr Ile Cys Asn Val Asn His
           195                    200                 205

Lys Pro Ser Asn Thr Lys Val Asp Lys Arg Val Glu Pro Lys Ser Cys
210                 215                   220

Asp Lys Thr His Thr Cys Pro Pro Cys Pro Ala Pro Glu Leu Leu Gly
225                 230              235             240

Gly Pro Ser Val Phe Leu Phe Pro Pro Lys Pro Lys Asp Thr Leu Met
           245                   250              255

Ile Ser Arg Thr Pro Glu Val Thr Cys Val Val Val Asp Val Ser His
           260                   265              270

Glu Asp Pro Glu Val Lys Phe Asn Trp Tyr Val Asp Gly Val Glu Val
           275                   280              285

His Asn Ala Lys Thr Lys Pro Arg Glu Glu Gln Tyr Asn Ala Thr Tyr
           290                   295              300

Arg Val Val Ser Val Leu Thr Val Leu His Gln Asp Trp Leu Asn Gly
305                 310              315             320

Lys Glu Tyr Lys Cys Lys Val Ser Asn Lys Ala Leu Pro Ala Pro Ile
           325                   330              335

Ala Ala Thr Ile Ser Lys Ala Lys Gly Gln Pro Arg Glu Pro Gln Val
           340                   345              350

Tyr Thr Leu Pro Pro Ser Arg Glu Glu Met Thr Lys Asn Gln Val Ser
           355                   360              365

Leu Thr Cys Leu Val Lys Gly Phe Tyr Pro Ser Asp Ile Ala Val Glu
           370                   375              380

Trp Glu Ser Asn Gly Gln Pro Glu Asn Asn Tyr Lys Thr Thr Pro Pro
385                 390              395             400

Val Leu Asp Ser Asp Gly Ser Phe Phe Leu Tyr Ser Lys Leu Thr Val
           405                   410              415

Asp Lys Ser Arg Trp Gln Gln Gly Asn Val Phe Ser Cys Ser Val Met
           420                   425              430

His Glu Ala Leu His Asn His Tyr Thr Gln Lys Ser Leu Ser Leu Ser
           435                   440              445

Pro Gly Lys
     450

```
<210> SEQ ID NO 7
<211> LENGTH: 645
<212> TYPE: DNA
<213> ORGANISM: Artificial Sequence
<220> FEATURE:
<223> OTHER INFORMATION: Light chain of anti-PD-L1 antibody IMM2515

<400> SEQUENCE: 7
gacattcaga tgacacagag ccctagcagc ctgagcgcaa gcgtgggcga cagagtgacc      60
atcacctgca gcaagccca agacatcatc aactacctga ctggtatca gcagaagcct     120 ggcaaggccc ctaagctgct gatctactac acaagcagac tgcacagcgg cgtgcctagc     180
agattcagcg gcagcggcag cggcaccgac ttcaccttca ccatcagcag cctgcagcct     240
gaggacatcg ccacctacta ctgtcagcaa ggcgacaccc tgccttggac cttcggccaa     300
ggcaccaagg tggagatcaa gcgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 8
<211> LENGTH: 214
<212> TYPE: PRT
<213> ORGANISM: Artificial Sequence
<220> FEATURE:
<223> OTHER INFORMATION: Light chain of anti-PD-L1 antibody IMM2515

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 1776
<212> TYPE: DNA
<213> ORGANISM: Artificial Sequence
<220> FEATURE:
<223> OTHER INFORMATION: SIRPaD1 mutant-linker-anti-PD-L1 heavy chain

<400> SEQUENCE: 9

```
gaggaggagc tgcaggtgat tcagcctgac aagtccgtat cagttgcagc tggagagtcg    60
gccattctgc actgcactgt gacctccctg atccctgtgg ggcccatcca gtggttcaga    120
ggagctggac cagcccggga attaatctac aatcaaaaag aaggccactt ccccgggta    180 acaactgttt cagagtccac aaagagagaa acatggact tttccatcag catcagtgcc    240
atcaccccag cagatgccgg cacctactac tgtgtgaagt tccggaaagg gagccctgac    300
acggagttta gtctggagc aggcactgag ctgtctgtgc gtgccaaacc ctctgccccc    360
```

```
gtggtatcgg gccctggcgg cggtgggagc ggcggcggtg ggagcggcgg cgggggctcg      420
caagtgcagc tggtgcagag cggcgccgag gtgaagaagc tggcgcaag cgtgaaggtg       480
agctgcaagg caagcggcta caccttcaca agcaactgga tgcactgggt gagacaagcc     540
cctggccaag gctggagtg gatgggcatg atccaccca cagcggcag cagcaactac        600
aacgagaagt tcaagagcag agtgaccatg acaagagaca caagcacaag accgtgtac     660
atggagctga gcagcctgag aagcgaggac accgccgtgt actactgcgc tagaagctac    720
tacggcagca gcccttacta cttcgactac tggggccaag gcaccctggt gaccgtgagc    780
agcgctagca ccaagggccc atcggtcttc cccctggcac cctcctccaa gagcacctct    840
gggggcacag cggccctggg ctgcctggtc aaggactact ccccgaacc ggtgacggtg      900
tcgtggaact caggcgccct gaccagcggc gtgcacacct tcccggctgt cctacagtcc    960
tcaggactct actccctcag cagcgtggtg accgtgccct ccagcagctt gggcacccag   1020
acctacatct gcaacgtgaa tcacaagccc agcaacacca aggtggacaa gagagttgag   1080
cccaaatctt gtgacaaaac tcacacatgc ccaccgtgcc cagcacctga actcctgggg   1140
ggaccgtcag tcttcctctt ccccccaaaa cccaaggaca cctcatgat ctcccggacc     1200
cctgaggtca catgcgtggt ggtggacgtg agccacgaag accctgaggt caagttcaac   1260
tggtatgtgg acggcgtgga ggtgcataat gccaagacaa agccgcggga ggagcagtac   1320
aacgccacgt accgtgtggt cagcgtcctc accgtcctgc accaagactg gctgaatggc   1380
aaggagtaca agtgcaaggt ctccaacaaa gccctcccag cccccatcgc cgcaaccatc   1440
tccaaagcca agggcagcc ccgagaacca caggtgtaca ccctgccccc atcccgggag    1500
gagatgacca gaaccaagt cagcctgacc tgcctggtca aaggcttcta tcccagcgac   1560
atcgccgtgg agtgggagag caatgggcag ccggagaaca actacaagac cacgcctccc   1620
gtgctggact ccgacggctc cttcttcctc tattccaagc tcaccgtgga caagagcagg   1680
tggcagcagg ggaacgtctt ctcatgctcc gtgatgcatg aggctctgca caaccactac   1740
acgcagaaga gcctctccct gtctccgggc aaatga                             1776
```

<210> SEQ ID NO 10
<211> LENGTH: 591
<212> TYPE: PRT
<213> ORGANISM: Artificial Sequence
<220> FEATURE:
<223> OTHER INFORMATION: SIRPaD1 mutant-linker-anti-PD-L1 heavy chain

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
        50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

```
Val Arg Ala Lys Pro Ser Ala Pro Val Val Ser Gly Pro Gly Gly
            115                 120                 125
Gly Ser Gly Gly Gly Ser Gly Gly Gly Ser Gln Val Gln Leu
    130                 135                 140
Val Gln Ser Gly Ala Glu Val Lys Lys Pro Gly Ala Ser Val Lys Val
145                 150                 155                 160
Ser Cys Lys Ala Ser Gly Tyr Thr Phe Thr Ser Asn Trp Met His Trp
                165                 170                 175
Val Arg Gln Ala Pro Gly Gln Gly Leu Glu Trp Met Gly Met Ile His
            180                 185                 190
Pro Asn Ser Gly Ser Ser Asn Tyr Asn Glu Lys Phe Lys Ser Arg Val
        195                 200                 205
Thr Met Thr Arg Asp Thr Ser Thr Ser Thr Val Tyr Met Glu Leu Ser
    210                 215                 220
Ser Leu Arg Ser Glu Asp Thr Ala Val Tyr Tyr Cys Ala Arg Ser Tyr
225                 230                 235                 240
Tyr Gly Ser Ser Pro Tyr Tyr Phe Asp Tyr Trp Gly Gln Gly Thr Leu
                245                 250                 255
Val Thr Val Ser Ser Ala Ser Thr Lys Gly Pro Ser Val Phe Pro Leu
            260                 265                 270
Ala Pro Ser Ser Lys Ser Thr Ser Gly Gly Thr Ala Ala Leu Gly Cys
        275                 280                 285
Leu Val Lys Asp Tyr Phe Pro Glu Pro Val Thr Val Ser Trp Asn Ser
    290                 295                 300
Gly Ala Leu Thr Ser Gly Val His Thr Phe Pro Ala Val Leu Gln Ser
305                 310                 315                 320
Ser Gly Leu Tyr Ser Leu Ser Ser Val Val Thr Val Pro Ser Ser Ser
                325                 330                 335
Leu Gly Thr Gln Thr Tyr Ile Cys Asn Val Asn His Lys Pro Ser Asn
            340                 345                 350
Thr Lys Val Asp Lys Arg Val Glu Pro Lys Ser Cys Asp Lys Thr His
        355                 360                 365
Thr Cys Pro Pro Cys Pro Ala Pro Glu Leu Leu Gly Gly Pro Ser Val
    370                 375                 380
Phe Leu Phe Pro Pro Lys Pro Lys Asp Thr Leu Met Ile Ser Arg Thr
385                 390                 395                 400
Pro Glu Val Thr Cys Val Val Val Asp Val Ser His Glu Asp Pro Glu
                405                 410                 415
Val Lys Phe Asn Trp Tyr Val Asp Gly Val Glu Val His Asn Ala Lys
            420                 425                 430
Thr Lys Pro Arg Glu Glu Gln Tyr Asn Ala Thr Tyr Arg Val Val Ser
        435                 440                 445
Val Leu Thr Val Leu His Gln Asp Trp Leu Asn Gly Lys Glu Tyr Lys
    450                 455                 460
Cys Lys Val Ser Asn Lys Ala Leu Pro Ala Pro Ile Ala Ala Thr Ile
465                 470                 475                 480
Ser Lys Ala Lys Gly Gln Pro Arg Glu Pro Gln Val Tyr Thr Leu Pro
                485                 490                 495
Pro Ser Arg Glu Glu Met Thr Lys Asn Gln Val Ser Leu Thr Cys Leu
            500                 505                 510
Val Lys Gly Phe Tyr Pro Ser Asp Ile Ala Val Glu Trp Glu Ser Asn
        515                 520                 525
```

-continued

Gly Gln Pro Glu Asn Asn Tyr Lys Thr Thr Pro Pro Val Leu Asp Ser
530                 535                 540

Asp Gly Ser Phe Phe Leu Tyr Ser Lys Leu Thr Val Asp Lys Ser Arg
545                 550                 555                 560

Trp Gln Gln Gly Asn Val Phe Ser Cys Ser Val Met His Glu Ala Leu
                565                 570                 575

His Asn His Tyr Thr Gln Lys Ser Leu Ser Leu Ser Pro Gly Lys
                580                 585                 590

<210> SEQ ID NO 11
<211> LENGTH: 1095
<212> TYPE: DNA
<213> ORGANISM: Artificial Sequence
<220> FEATURE:
<223> OTHER INFORMATION: SIRPaD1 mutant-Fc (IMM01)

<400> SEQUENCE: 11
gaggaggagc tgcaggtgat tcagcctgac aagtccgtat cagttgcagc tggagagtcg     60
gccattctgc actgcactgt gacctccctg atccctgtgg ggcccatcca gtggttcaga    120
ggagctggac cagcccggga attaatctac aatcaaaaag aaggccactt ccccgggta    180
acaactgttt cagagtccac aaagagagaa acatggact tttccatcag catcagtgcc    240
atcacccag cagatgccgg cacctactac tgtgtgaagt tccggaaagg gagccctgac    300
acggagttta gtctggagc aggcactgag ctgtctgtgc gtgccaaacc ctctgccccc    360
gtggtatcgg gcctgcggc gagggccaca cctcagcacg agcccaaatc ttgtgacaaa    420
actcacacat gcccaccgtg cccagcacct gaactcctgg ggggaccgtc agtcttcctc    480
ttcccccaa acccaagga caccctcatg atctcccgga cccctgaggt cacatgcgtg    540
gtggtggacg tgagccacga agaccctgag gtcaagttca actggtacgt ggacggcgtg    600
gaggtgcata atgccaagac aaagccgcgg gaggagcagt acaacagcac gtaccgtgtg    660
gtcagcgtcc tcaccgtcct gcaccaggac tggctgaatg gcaaggagta caagtgcaag    720
gtctccaaca agccctccc agccccatc gagaaaacca tctccaaagc caaagggcag    780
ccccgagaac cacaggtgta caccctgccc ccatcccggg atgagctgac caagaaccag    840
gtcagcctga cctgcctggt caaaggcttc tatcccagcg acatcgccgt ggagtgggag    900
agcaatgggc agccggagaa caactacaag accacgcctc ccgtgctgga ctccgacggc    960
tccttcttcc tctacagcaa gctcaccgtg gacaagagca ggtggcagca ggggaacgtc   1020
ttctcatgct ccgtgatgca tgaggctctg cacaaccact acacgcagaa gagcctctcc   1080
ctgtctccgg gttga                                                   1095

<210> SEQ ID NO 12
<211> LENGTH: 364
<212> TYPE: PRT
<213> ORGANISM: Artificial Sequence
<220> FEATURE:
<223> OTHER INFORMATION: SIRPaD1 mutant-Fc (IMM01)

<400> SEQUENCE: 12

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

```
Ile Tyr Asn Gln Lys Glu Gly His Phe Pro Arg Val Thr Val Ser
 50                  55                  60
Glu Ser Thr Lys Arg Glu Asn Met Asp Phe Ser Ile Ser Ile Ser Ala
 65                  70                  75                  80
Ile Thr Pro Ala Asp Ala Gly Thr Tyr Tyr Cys Val Lys Phe Arg Lys
                 85                  90                  95
Gly Ser Pro Asp Thr Glu Phe Lys Ser Gly Ala Gly Thr Glu Leu Ser
                100                 105                 110
Val Arg Ala Lys Pro Ser Ala Pro Val Val Ser Gly Pro Ala Ala Arg
                115                 120                 125
Ala Thr Pro Gln His Glu Pro Lys Ser Cys Asp Lys Thr His Thr Cys
130                 135                 140
Pro Pro Cys Pro Ala Pro Glu Leu Leu Gly Gly Pro Ser Val Phe Leu
145                 150                 155                 160
Phe Pro Pro Lys Pro Lys Asp Thr Leu Met Ile Ser Arg Thr Pro Glu
                165                 170                 175
Val Thr Cys Val Val Val Asp Val Ser His Glu Asp Pro Glu Val Lys
                180                 185                 190
Phe Asn Trp Tyr Val Asp Gly Val Glu Val His Asn Ala Lys Thr Lys
                195                 200                 205
Pro Arg Glu Glu Gln Tyr Asn Ser Thr Tyr Arg Val Val Ser Val Leu
210                 215                 220
Thr Val Leu His Gln Asp Trp Leu Asn Gly Lys Glu Tyr Lys Cys Lys
225                 230                 235                 240
Val Ser Asn Lys Ala Leu Pro Ala Pro Ile Glu Lys Thr Ile Ser Lys
                245                 250                 255
Ala Lys Gly Gln Pro Arg Glu Pro Gln Val Tyr Thr Leu Pro Pro Ser
                260                 265                 270
Arg Asp Glu Leu Thr Lys Asn Gln Val Ser Leu Thr Cys Leu Val Lys
                275                 280                 285
Gly Phe Tyr Pro Ser Asp Ile Ala Val Glu Trp Glu Ser Asn Gly Gln
                290                 295                 300
Pro Glu Asn Asn Tyr Lys Thr Thr Pro Pro Val Leu Asp Ser Asp Gly
305                 310                 315                 320
Ser Phe Phe Leu Tyr Ser Lys Leu Thr Val Asp Lys Ser Arg Trp Gln
                325                 330                 335
Gln Gly Asn Val Phe Ser Cys Ser Val Met His Glu Ala Leu His Asn
                340                 345                 350
His Tyr Thr Gln Lys Ser Leu Ser Leu Ser Pro Gly
                355                 360

<210> SEQ ID NO 13
<211> LENGTH: 57
<212> TYPE: DNA
<213> ORGANISM: Mus musculus

<400> SEQUENCE: 13
atgggatggt catgtatcat ccttttttctg gtagcaactg caactggagt acattca     57

<210> SEQ ID NO 14
<211> LENGTH: 9
<212> TYPE: DNA
<213> ORGANISM: Artificial Sequence
<220> FEATURE:
<223> OTHER INFORMATION: Kozak

<400> SEQUENCE: 14
```

```
gccgccacc                                                              9
```

<210> SEQ ID NO 15
<211> LENGTH: 1204
<212> TYPE: DNA
<213> ORGANISM: Artificial Sequence
<220> FEATURE:
<223> OTHER INFORMATION: SIRPaD1 mutant-linker-anti-PD-L1 light chain

<400> SEQUENCE: 15

```
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt ccccccgggta    180
acaactgttt cagagtccac aaagagagaa acatggact tttccatcag catcagtgcc     240
atcaccccag cagatgccgg cacctactac tgtgtgaagt tccggaaagg gagccctgac    300
acggagttta gtctggagc aggcactgag ctgtctgtgc gtgccaaacc ctctgccccc    360
gtggtatcgg gccctggcgg cggtgggagc ggcggcggtg ggagcggcgg cggggctcg     420
gacattcaga tgacacagag ccctagcagc ctgagcgcaa gcgtgggcga cagagtgacc    480
atcacctgca gagcaagcca agacatcatc aactacctga actggtatca gcagaagcct    540
ggcaaggccc ctaagctgct gatctactac acaagcagac tgcacagcgg cgtgcctagc    600
agattcagcg gcagcggcag cggcaccgac ttcaccttca ccatcagcag cctgcagcct    660
gaggacatcg ccacctacta ctgtcagcaa ggcgacaccc tgccttggac cttcggccaa    720
ggcaccaagg tggagatcaa gcgtgagttc tagaggatcc atctgggata agcatgctgt    780
tttctgtctg tccctaacat gccctgtgat tatccgcaaa caacacaccc aagggcagaa    840
cttttgttact taaacaccat cctgtttgct tctttcctca ggaactgtgg ctgcaccatc    900
tgtcttcatc ttcccgccat ctgatgagca gttgaaatct ggaactgcct ctgttgtgtg    960
cctgctgaat aacttctatc ccagagaggc caaagtacag tggaaggtgg ataacgccct   1020
ccaatcgggt aactcccagg agagtgtcac agagcaggac agcaaggaca gcacctacag   1080
cctcagcagc accctgacgc tgagcaaagc agactacgag aaacacaaag tctacgcctg   1140
cgaagtcacc catcagggcc tgagctcgcc cgtcacaaag agcttcaaca ggggagagtg   1200
ttag                                                                1204
```

<210> SEQ ID NO 16
<211> LENGTH: 354
<212> TYPE: PRT
<213> ORGANISM: Artificial Sequence
<220> FEATURE:
<223> OTHER INFORMATION: SIRPaD1 mutant-linker-anti-PD-L1 light chain

<400> SEQUENCE: 16

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80
```

-continued

```
Ile Thr Pro Ala Asp Ala Gly Thr Tyr Tyr Cys Val Lys Phe Arg Lys
                85                  90                  95
Gly Ser Pro Asp Thr Glu Phe Lys Ser Gly Ala Gly Thr Glu Leu Ser
            100                 105                 110
Val Arg Ala Lys Pro Ser Ala Pro Val Val Ser Gly Pro Gly Gly Gly
        115                 120                 125
Gly Ser Gly Gly Gly Gly Ser Gly Gly Gly Gly Ser Asp Ile Gln Met
    130                 135                 140
Thr Gln Ser Pro Ser Ser Leu Ser Ala Ser Val Gly Asp Arg Val Thr
145                 150                 155                 160
Ile Thr Cys Arg Ala Ser Gln Asp Ile Ile Asn Tyr Leu Asn Trp Tyr
                165                 170                 175
Gln Gln Lys Pro Gly Lys Ala Pro Lys Leu Leu Ile Tyr Tyr Thr Ser
            180                 185                 190
Arg Leu His Ser Gly Val Pro Ser Arg Phe Ser Gly Ser Gly Ser Gly
        195                 200                 205
Thr Asp Phe Thr Phe Thr Ile Ser Ser Leu Gln Pro Glu Asp Ile Ala
    210                 215                 220
Thr Tyr Tyr Cys Gln Gln Gly Asp Thr Leu Pro Trp Thr Phe Gly Gln
225                 230                 235                 240
Gly Thr Lys Val Glu Ile Lys Arg Thr Val Ala Ala Pro Ser Val Phe
                245                 250                 255
Ile Phe Pro Pro Ser Asp Glu Gln Leu Lys Ser Gly Thr Ala Ser Val
            260                 265                 270
Val Cys Leu Leu Asn Asn Phe Tyr Pro Arg Glu Ala Lys Val Gln Trp
        275                 280                 285
Lys Val Asp Asn Ala Leu Gln Ser Gly Asn Ser Gln Glu Ser Val Thr
    290                 295                 300
Glu Gln Asp Ser Lys Asp Ser Thr Tyr Ser Leu Ser Ser Thr Leu Thr
305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
            340                 345                 350
Glu Cys

<210> SEQ ID NO 17
<211> LENGTH: 10
<212> TYPE: PRT
<213> ORGANISM: Artificial Sequence
<220> FEATURE:
<223> OTHER INFORMATION: Linker

<400> SEQUENCE: 17

Gly Gly Gly Gly Ser Gly Gly Gly Gly Ser
1               5                   10

<210> SEQ ID NO 18
<211> LENGTH: 20
<212> TYPE: PRT
<213> ORGANISM: Artificial Sequence
<220> FEATURE:
<223> OTHER INFORMATION: Linker

<400> SEQUENCE: 18

Gly Gly Gly Gly Ser Gly Gly Gly Gly Ser Gly Gly Gly Gly Ser Gly
1               5                   10                  15
```

Gly Gly Gly Ser
            20

<210> SEQ ID NO 19
<211> LENGTH: 121
<212> TYPE: PRT
<213> ORGANISM: Artificial Sequence
<220> FEATURE:
<223> OTHER INFORMATION: Heavy chain variable region of anti-PD-L1
      antibody IMM2515

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Arg Gln Ala Pro Gly Gln Gly Leu Glu Trp Met
        35                  40                  45

Gly Met Ile His Pro Asn Ser Gly Ser Ser Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Gly Ser Ser Pro Tyr Tyr Phe Asp Tyr Trp Gly
            100                 105                 110

Gln Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: Light chain variable region of anti-PD-L1
      antibody IMM2515

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Thr Leu Pro Trp
                85                  90                  95

Thr Phe Gly Gln Gly Thr Lys Val Glu Ile Lys
            100                 105

<210> SEQ ID NO 21
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 21

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ala Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Ala Ala Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 22
<211> LENGTH: 391
<212> TYPE: PRT
<213> ORGANISM: Artificial Sequence
<220> FEATURE:
<223> OTHER INFORMATION: Human PD-1-mouse IgG1 Fc

<400> SEQUENCE: 22

```
Met Gly Trp Ser Cys Ile Ile Leu Phe Leu Val Ala Thr Ala Thr Gly
1               5                   10                  15
Val His Ser Leu Asp Ser Pro Asp Arg Pro Trp Asn Pro Pro Thr Phe
```

20                  25                  30
Ser Pro Ala Leu Leu Val Val Thr Glu Gly Asp Ala Ala Thr Phe Thr
                35                  40                  45
Cys Ser Phe Ser Asn Thr Ser Glu Ser Phe Val Leu Asn Trp Tyr Arg
         50                  55                  60
Met Ser Pro Ser Asn Gln Thr Asp Lys Leu Ala Ala Phe Pro Glu Asp
 65                  70                  75                  80
Arg Ser Gln Pro Gly Gln Asp Cys Arg Phe Arg Val Thr Gln Leu Pro
                 85                  90                  95
Asn Gly Arg Asp Phe His Met Ser Val Val Arg Ala Arg Arg Asn Asp
                100                 105                 110
Ser Gly Thr Tyr Leu Cys Gly Ala Ile Ser Leu Ala Pro Lys Ala Gln
                115                 120                 125
Ile Lys Glu Ser Leu Arg Ala Glu Leu Arg Val Thr Glu Arg Arg Ala
            130                 135                 140
Glu Val Pro Thr Ala His Pro Ser Pro Ser Pro Arg Pro Ala Gly Gln
145                 150                 155                 160
Phe Gln Glu Phe Val Pro Arg Asp Cys Gly Cys Lys Pro Cys Ile Cys
                165                 170                 175
Thr Val Pro Glu Val Ser Ser Val Phe Ile Phe Pro Pro Lys Pro Lys
                180                 185                 190
Asp Val Leu Thr Ile Thr Leu Thr Pro Lys Val Thr Cys Val Val Val
            195                 200                 205
Asp Ile Ser Lys Asp Asp Pro Glu Val Gln Phe Ser Trp Phe Val Asp
        210                 215                 220
Asp Val Glu Val His Thr Ala Gln Thr Gln Pro Arg Glu Glu Gln Phe
225                 230                 235                 240
Asn Ser Thr Phe Arg Ser Val Ser Glu Leu Pro Ile Met His Gln Asp
                245                 250                 255
Trp Leu Asn Gly Lys Glu Phe Lys Cys Arg Val Asn Ser Ala Ala Phe
                260                 265                 270
Pro Ala Pro Ile Glu Lys Thr Ile Ser Lys Thr Lys Gly Arg Pro Lys
            275                 280                 285
Ala Pro Gln Val Tyr Thr Ile Pro Pro Lys Glu Gln Met Ala Lys
        290                 295                 300
Asp Lys Val Ser Leu Thr Cys Met Ile Thr Asp Phe Phe Pro Glu Asp
305                 310                 315                 320
Ile Thr Val Glu Trp Gln Trp Asn Gly Gln Pro Ala Glu Asn Tyr Lys
                325                 330                 335
Asn Thr Gln Pro Ile Met Asn Thr Asn Gly Ser Tyr Phe Val Tyr Ser
            340                 345                 350
Lys Leu Asn Val Gln Lys Ser Asn Trp Glu Ala Gly Asn Thr Phe Thr
        355                 360                 365
Cys Ser Val Leu His Glu Gly Leu His Asn His His Thr Glu Lys Ser
    370                 375                 380
Leu Ser His Ser Pro Gly Lys
385                 390

<210> SEQ ID NO 23
<211> LENGTH: 602
<212> TYPE: PRT
<213> ORGANISM: Artificial Sequence
<220> FEATURE:
<223> OTHER INFORMATION: Wild type human SIRPaD1-human IgG1 Fc

<400> SEQUENCE: 23

```
Met Gly Trp Ser Cys Ile Ile Leu Phe Leu Val Ala Thr Ala Thr Gly
1               5                   10                  15

Val His Ser Ser Cys Ala Trp Ser Gly Val Ala Gly Glu Glu Glu Leu
            20                  25                  30

Gln Val Ile Gln Pro Asp Lys Ser Val Ser Val Ala Ala Gly Glu Ser
        35                  40                  45

Ala Ile Leu His Cys Thr Val Thr Ser Leu Ile Pro Val Gly Pro Ile
    50                  55                  60

Gln Trp Phe Arg Gly Ala Gly Pro Ala Arg Glu Leu Ile Tyr Asn Gln
65                  70                  75                  80

Lys Glu Gly His Phe Pro Arg Val Thr Thr Val Ser Glu Ser Thr Lys
                85                  90                  95

Arg Glu Asn Met Asp Phe Ser Ile Ser Ile Ser Asn Ile Thr Pro Ala
            100                 105                 110

Asp Ala Gly Thr Tyr Tyr Cys Val Lys Phe Arg Lys Gly Ser Pro Asp
        115                 120                 125

Thr Glu Phe Lys Ser Gly Ala Gly Thr Glu Leu Ser Val Arg Ala Lys
    130                 135                 140

Pro Ser Ala Pro Val Val Ser Gly Pro Ala Ala Arg Ala Thr Pro Gln
145                 150                 155                 160

His Thr Val Ser Phe Thr Cys Glu Ser His Gly Phe Ser Pro Arg Asp
                165                 170                 175

Ile Thr Leu Lys Trp Phe Lys Asn Gly Asn Glu Leu Ser Asp Phe Gln
            180                 185                 190

Thr Asn Val Asp Pro Val Gly Glu Ser Val Ser Tyr Ser Ile His Ser
        195                 200                 205

Thr Ala Lys Val Val Leu Thr Arg Glu Asp Val His Ser Gln Val Ile
    210                 215                 220

Cys Glu Val Ala His Val Thr Leu Gln Gly Asp Pro Leu Arg Gly Thr
225                 230                 235                 240

Ala Asn Leu Ser Glu Thr Ile Arg Val Pro Pro Thr Leu Glu Val Thr
                245                 250                 255

Gln Gln Pro Val Arg Ala Glu Asn Gln Val Asn Val Thr Cys Gln Val
            260                 265                 270

Arg Lys Phe Tyr Pro Gln Arg Leu Gln Leu Thr Trp Leu Glu Asn Gly
        275                 280                 285

Asn Val Ser Arg Thr Glu Thr Ala Ser Thr Val Thr Glu Asn Lys Asp
    290                 295                 300

Gly Thr Tyr Asn Trp Met Ser Trp Leu Leu Val Asn Val Ser Ala His
305                 310                 315                 320

Arg Asp Asp Val Lys Leu Thr Cys Gln Val Glu His Asp Gly Gln Pro
                325                 330                 335

Ala Val Ser Lys Ser His Asp Leu Lys Val Ser Ala His Pro Lys Glu
            340                 345                 350

Gln Gly Ser Asn Thr Ala Ala Glu Asn Thr Gly Ser Asn Glu Arg Asn
        355                 360                 365

Glu Phe Glu Pro Lys Ser Cys Asp Lys Thr His Thr Cys Pro Pro Cys
    370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415
```

-continued

```
Val Val Val Asp Val Ser His Glu Asp Pro Glu Val Lys Phe Asn Trp
            420             425             430
Tyr Val Asp Gly Val Glu Val His Asn Ala Lys Thr Lys Pro Arg Glu
        435             440             445
Glu Gln Tyr Asn Ser Thr Tyr Arg Val Val Ser Val Leu Thr Val Leu
    450             455             460
His Gln Asp Trp Leu Asn Gly Lys Glu Tyr Lys Cys Lys Val Ser Asn
465             470             475             480
Lys Ala Leu Pro Ala Pro Ile Glu Lys Thr Ile Ser Lys Ala Lys Gly
                485             490             495
Gln Pro Arg Glu Pro Gln Val Tyr Thr Leu Pro Pro Ser Arg Asp Glu
            500             505             510
Leu Thr Lys Asn Gln Val Ser Leu Thr Cys Leu Val Lys Gly Phe Tyr
        515             520             525
Pro Ser Asp Ile Ala Val Glu Trp Glu Ser Asn Gly Gln Pro Glu Asn
    530             535             540
Asn Tyr Lys Thr Thr Pro Pro Val Leu Asp Ser Asp Gly Ser Phe Phe
545             550             555             560
Leu Tyr Ser Lys Leu Thr Val Asp Lys Ser Arg Trp Gln Gln Gly Asn
                565             570             575
Val Phe Ser Cys Ser Val Met His Glu Ala Leu His Asn His Tyr Thr
            580             585             590
Gln Lys Ser Leu Ser Leu Ser Pro Gly Lys
        595             600
```